(12) United States Patent
Monforte

(10) Patent No.: US 7,824,856 B2
(45) Date of Patent: Nov. 2, 2010

(54) EXPRESSION PROFILING USING MICROARRAYS

(75) Inventor: Joseph Monforte, Kensington, CA (US)

(73) Assignee: Althea Technologies, Inc., San Diego, CA (US)

( * ) Notice: Subject to any disclaimer, the term of this patent is extended or adjusted under 35 U.S.C. 154(b) by 597 days.

(21) Appl. No.: 10/938,130

(22) Filed: Sep. 10, 2004

(65) Prior Publication Data

US 2005/0170373 A1 Aug. 4, 2005

Related U.S. Application Data

(60) Provisional application No. 60/502,108, filed on Sep. 10, 2003, provisional application No. 60/538,283, filed on Jan. 21, 2004.

(51) Int. Cl.
*C12Q 1/68* (2006.01)
(52) U.S. Cl. .......................................................... 435/6
(58) Field of Classification Search ....................... None
See application file for complete search history.

(56) References Cited

U.S. PATENT DOCUMENTS

| | | | |
|---|---|---|---|
| 5,143,854 A | 9/1992 | Pirrung et al. | |
| 5,545,522 A | 8/1996 | Van Gelder et al. | |
| 5,595,895 A | 1/1997 | Miki et al. | |
| 5,807,522 A | 9/1998 | Brown et al. | |
| 5,882,856 A | 3/1999 | Shuber | |
| 5,935,793 A | 8/1999 | Wong | |
| 5,962,271 A | 10/1999 | Chenchik et al. | |
| 6,087,102 A | 7/2000 | Chenchik et al. | |
| 6,207,372 B1 | 3/2001 | Shuber | |
| 6,251,639 B1 | 6/2001 | Kurn | |
| 6,258,536 B1 * | 7/2001 | Oliner et al. ................ | 435/6 |
| 6,287,765 B1 | 9/2001 | Cubicciotti | |
| 6,287,768 B1 | 9/2001 | Chenchik et al. | |
| 6,406,840 B1 | 6/2002 | Li et al. | |
| 6,458,566 B2 | 10/2002 | Alland et al. | |
| 6,489,159 B1 | 12/2002 | Chenchik et al. | |
| 6,495,320 B1 | 12/2002 | Lockhart et al. | |
| 6,500,620 B2 | 12/2002 | Yu et al. | |
| 6,500,938 B1 | 12/2002 | Au-Young et al. | |
| 6,562,567 B2 | 5/2003 | Wold | |
| 6,607,885 B1 | 8/2003 | Larossa et al. | |
| 6,618,679 B2 | 9/2003 | Loehrlein et al. | |
| 7,226,734 B2 * | 6/2007 | Chee et al. .................. | 435/6 |
| 2001/0026919 A1 | 10/2001 | Chenchik et al. | |
| 2002/0037510 A1 | 3/2002 | Ness et al. | |
| 2002/0142313 A1 | 10/2002 | Wolber et al. | |

FOREIGN PATENT DOCUMENTS

| | | |
|---|---|---|
| WO | WO 97/27317 A1 | 7/1997 |
| WO | WO 99/35289 A1 | 7/1999 |
| WO | WO 01/55454 A1 | 8/2001 |
| WO | WO 01/71023 A1 | 9/2001 |
| WO | WO 02/08466 A1 | 1/2002 |
| WO | WO 02/40717 A2 | 5/2002 |
| WO | WO 02/101358 A2 | 12/2002 |
| WO | WO 2004/009765 A2 | 1/2004 |

OTHER PUBLICATIONS

Shepard and Cooper (2000) Mod. PAthol. 13(4):401-406.*
Shepard and Cooper (2000) "Assessing the Expression of Two Genes Simultaneously in Surgical Specimens Using Polymerase Chain Reaction." *Modern Pathology* 13(4): 401-406.
Fan et al., "A Versatile Assay for High-Throughput Gene Expression Profiling on Universal Array Matrices", Genome Research, Cold Spring Harbor Lab. Press, vol. 4, No. 5. [ages 878-885 (2004).
Osiowy et al. (1998) "Direct Detection of Respiratory Syncytial Virus, Parainfluenza Virus, and Adenovirus in Clinical Respiratory Specimens by a Mutliplex Reverse Transcription-PCR Assay." *Journal of Clilnical Microbiology*, 36(11): 3149-3454.
Pegasus Scientific printout Jan. 31, 2010.
Peng et al. (1996) "Replication Error Phenotype and p53 Gene Mutation in Lymphomas of Musoca-Associated Lymphoid Tissue." *American Journal of Pathology*, 148(2): 643-648.
Recchi et al. (1998) "Mutiplex RT-PR method for the analysis of the expression of human sialyltransferases: application to breast cancer cells." *Glycoconjugate Journal*, 15: 19-27.
Shuber et al. (1997) "High throughput parallel analysis of hundreds of patient samples for more than 100 mutations in multiple disease genes." *Human Molecular Genetics*, 6(3): 337-347.
Walker et al. (1998) "Effects of Prolactin in Stimulating Disease Activity in Systemic Lupus Erythematosus." *Annals of New York Academy of Sciences*, 840: 762-772.
White and Bancroft (1982) Simple Alalysis fo Relative mRNA Levels in Multiple Small Cell or Tissue Smaples. *The Journal of Biological Chemistry*, 357(15): 8569-8572.
Eberwine (1996) "Amplifications of mRNA Populations Using aRNA Generated from Immobilized Oligo (dT)-T7 Primed cDNA." *Biotechniques* 20: 584-591.
Fodor et al. (1991) "Light-Directed Spatially Addressable Parallel Chemical Synthesis." *Science* 251:767-773.
Puskas et al. "RNA Amplification Results in Reproducible Microarray Data with Slight Ratio Bias." *Biotechniques* 32(6): 1330-1334, (2002).

(Continued)

*Primary Examiner*—Christopher M. Babic
(74) *Attorney, Agent, or Firm*—Christina Onufryk; Stacy Landry; Quine Intellectual Property Law Group, P.C.

(57) ABSTRACT

The invention provides novel compositions and methods for the analysis of gene expression (e.g., expression profiling) using microarray-based technology. In some embodiments of the invention, the novel methods use gene-specific as well as universal amplification primers during sample preparation, and the methods permit the simultaneous analysis of multiple samples on the same microarray. Furthermore, some embodiments of the invention incorporate barcode sequences into the amplified products, thereby permitting the use of generic arrays and generic labeled probes.

4 Claims, 10 Drawing Sheets

OTHER PUBLICATIONS

Schena et al. (1995) "Quantitative Monitoring of Gene Expression Patterns with a Complementary DNA Microarray." *Science* 270:467-470.

Thomas et al. (2001) "Identification of Toxicologically Predictive Gene Sets Using cDNA Microarrays." *Molecular Pharmacology* 60: 1189-1194.

Van't Veer et al. (2002) "Gene Expression Profiling Predicts Clinical Outcome of Breast Cancer." *Nature* 415: 530-536.

Van Gelder et al. (1990) "Amplified RNA Synthesized from Limited Quantities of Heterogeneous cDNA." *Proceeding of the National Academy of Sciences* USA 87(5): 1663-1667.

Chung et al. (2004) "A Study on the Effects of Degradation and Template Concentration on the Amplification Efficiency of the STR Miniplex Primer Sets." *Journal of Forensic Science*, 49(4): 733-740.

Clavel et al. (1998) "DNA-EIA to detect high and low risk HPV genotypes in cervical lesions with E6/E7 primer mediated multiplex PCR." *Journal of Clinical Pathology*, 51: 38-43.

Fan and Hendrickson (1996) "Rapid Diagnosis of Human Parainfluenza Virus Type 1 Infection by Quantitative Reverse Transcription-PCR-Enzyme Hybridization Assay." *Journal of Clinical Microbiology*, 34(8): 1914-1917.

Neilan et al. (1997) A universal procedure for primer labeling of amplifications. *Nucleic Acids Research*, 25(14): 2938-2939.

Yu et al. (1997) "Specific Inhibition of PCR by Non-Extendable Oligonucleotide Using a 5' to 3' Exonuclease-Deficient DNA Polymerase." *Bio Technoques*, 23(4): 714-720.

\* cited by examiner

EXPRESSION PROFILING USING MICROARRAYS

This invention claims priority to and benefit of U.S. Provisional Patent Application Ser. No. 60/502,108, filed Sep. 10, 2003; and U.S. Provisional Patent Application Ser. No. 60/538,283, filed Jan. 21, 2004.

FIELD OF THE INVENTION

The invention pertains to the field of gene expression analysis. The invention provides novel compositions and methods for the analysis of gene expression using microarray-based technology.

BACKGROUND OF THE INVENTION

The pace at which the genetics of disease states are being deciphered has been accelerating. For example, researchers have begun to characterize in detail multiple genetic mechanisms that give rise to cancer, as well as numerous functional pathways associated with cancer such as damage response, cell cycle, cell proliferation and cell death. This exponential growth in our knowledge base of cancer genetics has led to the identification of a large array of genes, proteins and pathways that potentially play a central role in carcinogenesis and/or may be potential targets for therapeutic intervention. The challenge now is to experimentally delve deeper, both into how these genes function and interrelate in vivo and in vitro, as well as into how different compounds and compound classes influence these genes.

Over the last decade, gene expression analysis has proven to be an extremely valuable tool for monitoring the physiologic state of cells and specific pathway responses to different stimuli and environments. This ability to both broadly survey cellular activities and to track differential and dynamic responses suggests that expression tools have been able to provide significant insight into cancer genetics. The current state of the art in large-scale gene expression analysis is the microarray.

Microarrays enable large-scale surveys of thousands of genes for small sets of samples. However, current microarray sample labeling methods are quite costly, e.g. $100 per sample, limiting the number of samples that can be analyzed in microarray format for a given budget. Current labeling methods also require relatively large quantities of RNA (e.g. multiple micrograms of RNA), which limits the types of sources for which RNA analysis can be performed. Several amplification schemes have been developed to compensate for this sample size limitation, including SMART™ technology from BD Clontech (Palo Alto, Calif.), Ovation™ amplification from NuGEN Technologies, Inc. (San Carlos, Calif.), and RiboAmp® RNA amplification kits from Arcturus, Inc. (Mountain View, Calif.), but they all add additional sample handling steps and expense to the reagent cost for each sample. In addition, all of these methods are global amplification schemes that randomly amplify all of the RNA transcripts in the sample. This global amplification, which amplifies all genes (i.e., transcripts) in a sample results in each individual gene being represented in a relatively low ratio relative to all of the remaining amplified transcripts in the sample.

Furthermore, there is a growing trend in gene expression analysis for screening moderate sets of genes, e.g., screening tens to hundreds of genes for hundreds to thousands of samples. For example, to fully capture the activities of functional pathways such as apoptosis or angiogenesis, it is desirable to track between 50 and 100 genes. In fact, linear and nonlinear statistical techniques have been successfully applied to the analysis of microarray data and it is clear that correlation and cluster analysis generally collapses the responses of thousands of genes to a much smaller set of representative genes and response types. For example, Thomas et.al. (Molecular Pharmacology (2001) 60(6):1189-1194) have used this approach to identify 12 key transcripts out of 1200 that can predictively track five major toxicological responses. Also, for example, van't Veer et.al. (Nature (2002) 415:530-536) recently suggested that a set of 70 genes, out of 25,000 tested, could provide a prognostic signature for metastases in breast cancer patients, and that the expression profile outperformed other clinical parameters used to predict disease outcome.

Another major area of interest for a high throughput gene expression assay is compound library screening. The predominant screening assay formats used today fall into two categories: gene specific and phenotypic. Gene-specific screens, such as protein binding assays and reporter gene assays, focus on capturing the effects of a given compound on a single gene or protein endpoint, while phenotypic screens typically capture gross cellular changes such as apoptosis, cell proliferation or ion flux. Both of these screening approaches have significant value, but they are not optimal for screening compounds and how they impact the multiplicity of genes involved in a complex disease like cancer. Gene-specific screens are too focused and cannot observe multigenic responses to perturbations. Cell-based phenotypic screens are too broad and cannot be used to differentiate the multiple pathways that can be altered to produce a phenotypic response nor can they effectively be used to optimize and direct compound development toward specific mechanisms of action. The utilization of a screen that can look at a multiplicity of genes in parallel, e.g. 10-100, can be used to overcome the deficits of these other screening approaches.

While existing microarray methodologies could be pressed into service in these important experimental areas, the fact of the matter is that they cannot not be used because of practical economics associated with the analysis of a large number of samples and minimal quantities of RNA. The present invention addresses these and other concerns as will be apparent upon review of the attached disclosure.

SUMMARY OF THE INVENTION

The invention provides a variety of novel compositions and methods for gene expression profiling. The inventions taught herein combine microarray technology with techniques for the amplification of subsets of transcripts in an RNA sample, gene-specific primers, and universal primers that amplify all or a subset of transcripts in a sample. Some embodiments of the invention incorporate barcode sequences into the RNA sample amplification products, thereby adding a powerful tool that permits the use (and reuse) of "generic arrays" and generic labeled probes. The compositions and methods of the invention also permit the simultaneous analysis of multiple amplified RNA samples. Novel compositions and methods of the invention are also appealing in view of their elimination for the necessity to globally label an amplified RNA sample and represent potential cost-savings.

The invention provides methods for the parallel analysis of multiple amplified RNA nucleic acid samples, where the samples incorporate a specified barcode sequence. In some aspects, this barcode is the means by which the nucleic acid sample is arrayed onto a array platform for expression profiling. These methods permit the simultaneous detection of a plurality of expression products from a plurality of biological samples, where the steps of the methods include, (a) obtaining a plurality of expressed RNA samples each comprising a plurality of polynucleotide sequences (e.g., expressed gene sequences) from each of a plurality of biological samples; (b) introducing at least one barcode sequence into a plurality of replicate nucleic acids corresponding to at least a subset of the plurality of polynucleotide sequences of the expressed RNA samples; (c) applying the plurality of replicate nucleic acids to an array to produce a nucleic acid array; and (d) detecting a plurality of signals corresponding to arrayed replicate nucleic acids.

In some aspects, an identical barcode is introduced into each of the plurality of replicate nucleic acids of an expressed RNA sample. Alternatively, a different barcode is introduced into each of the replicate nucleic acids corresponding to a different polynucleotide sequence (e.g., an expressed gene sequence) of the subset. The replicate nucleic acids can be produced by reverse transcription, or any other suitable method for amplification. In some aspects, the replicate nucleic acids are produced by selective amplification of the plurality of expressed RNA samples, for example, by one or more of the techniques PCR, TMA, NASBA and RCA. Most typically, amplification, including the selective amplification, is performed by PCR. The selective amplification can be performed in a multiplex reaction using a plurality of gene specific primers. Optionally, the gene specific primers include a universal priming sequence and/or a barcode sequence. Optionally, the primer with the universal priming sequence also carries a detectable moiety, such as a fluorescent label.

In some embodiments, the invention provides methods for constructing the arrays of samples by using defined sequence probes (typically where the probes are anchored to a solid substrate (e.g., a glass surface). In some aspects, arrays of replicate nucleic acids (e.g., those derived from RNA samples) are arrayed by hybridizing them to an array of defined sequence probes. In some aspects, the arraying of the sample(s) is by hybridizing them to an array comprising polynucleotide sequences that hybridize to a barcode sequence introduced into the amplified nucleic acid samples. In some aspectss, the replicate nucleic acids are arrayed, and optionally, are pooled for arraying.

In some embodiments, the selective amplification of the RNA sample amplifies between about 5 and about 100 polynucleotide sequences, or optionally, between about 10 and about 50 polynucleotide sequences. In some aspects, each expressed RNA sample is amplified in two or more target specific amplification reactions and spatially arrayed the resulting amplification products in two or more locations on an array. In some aspects, two or more barcode sequence are incorporated into the plurality of replicate nucleic acids.

In the methods described herein, the arrayed nucleic acid can be detected by hybridizing a defined sequence probe comprising a detectable moiety. In this aspect, a plurality of defined sequence probes with different polynucleotide sequences are hybridized to the nucleic acid array, where each probe is capable of generating a different detectable signal. In some aspects, at least one arrayed nucleic acid is detected by hybridizing a barcode specific probe carrying a detectable moiety. The detectable moiety can be a fluorescent label. In the case where a plurality of probes are used, each probe uses a different fluorescent label. In some aspects, the arrayed nucleic acid is detected by hybridizing a linking oligonucleotide with at least a first subsequence that hybridizes to a gene specific sequence and at least a second subsequence carrying a barcode sequence, and then hybridizing a probe with a detectable moiety to the barcode sequence.

In some embodiments, the plurality of expressed RNA samples are from biological samples that have been contacted with at least one member of a compound library. In some aspects, the detected signal from the probe on the array is quantitated, and optionally, the quantitated signal is compared to a control signal. In some aspects, the quantitated signal is increased or decreased relative to the control signal. The detected quantitated signal that is different from a control signal can be analyzed using at least one statistical analysis. Is some aspects, the biological samples can be tissue, a tissue extract, a primary cell isolate or cells grown in culture. The biological samples can include one or more cell lines. Where multiple biological samples are used, each sample can be contacted with a member of a compound library prior to collection of the expressed RNA sample. In some aspects, each biological sample is contacted with a different member of the compound library.

In some embodiments, expression of one or more genes in one or more cell lines used to derive RNA samples is artificially altered prior to treating with a member of a compound library using a procedure selected from insertional mutagenesis, deletion of genomic DNA, targeted gene disruption, transcription blocking, introduction of a genomic or episomal vector, antisense DNA or RNA, ribozymes, iRNA, DNA binding oligonucleotides, and zinc finger proteins.

Biological samples used to derive RNA samples can use eukaryotic or prokaryotic cells. The compound library used to treat cells prior to collecting an RNA sample can use a compound collection library, a combinatorial chemical library, a scaffold-focused chemical library, a target focused chemical library, an antibody library, a biological library, a natural product library, an antisense agent library, an iRNA library, a siRNA library, a ribozyme library, a peptide library, or a combinatorial nucleic acid oligomer library. In some aspects, expressed RNA samples are obtained from at least 500 biological samples, alternatively, from at least 1000 biological samples, or alternatively from at least 10,000 biological samples. In some embodiments, the expressed RNA samples are collected by isolating total cellular RNA. Alternatively, messenger RNA (mRNA) can be isolated. In some aspects, a plurality of RNAs, cDNAs or amplified nucleic acids corresponding to the expressed RNA samples are arrayed. Where multiple samples are arrayed, the amplified nucleic acids can be produced by selective amplification of the plurality of expressed RNA samples.

In some embodiments of the invention, the arraying and gene profiling strategy includes (i) hybridizing at least a first defined sequence probe and at least a second defined sequence probe, where the first defined sequence probe hybridizes to a housekeeping gene and where at least a second defined sequence probe hybridizes to a target sequence; (ii) quantitating the hybridization signals for the first and at least second defined sequence probes; and, (iii) determining the expression of the at least second defined sequence probe relative to the first defined sequence probe. In such methods, the nucleic acids corresponding to the expressed RNA samples can be arrayed in two or more duplicate arrays, and each array is hybridized to the first defined sequence probe and the least a second defined sequence probe, where the first defined sequence probe is the same between the two or more duplicate arrays and the at least second defined sequence probe differs between the two or more duplicate arrays.

In some embodiments, the plurality of defined sequence probes used in an array(s) can comprise a set of disease related target genes. Furthermore, a variety of array formats and materials are well-known to one of skill in the art. In some aspects, arraying the nucleic acids is on a solid phase surface. In some aspects, the nucleic acids are arrayed on a two dimensional solid phase surface, on a plurality of solid phase surfaces, for example, where the solid phase surfaces can be beads, spheres or optical fibers. A solid phase surface can incorporate glass, coated glass, silicon, porous silicon, nylon, ceramic or plastic. Similarly, the defined sequence is not limited to any particular base sequence or nucleic acid structure. For example, the defined sequence probes can be one or more synthetic probes, for example, an oligonucleotide, a cDNA; an amplification product, or a restriction fragment. The defined sequence probes capable of generating a detectable signal can incorporate, for example, a fluorescent label, a chromophore, an electrophore, a radioactive nuclide, a chemically reactive moiety, an amplifiable signal element or a ligand capable of binding to an enzyme. In some aspects, the amplifiable signal element is an oligonucleotide. In some aspects, the oligonucleotide amplifiable signal element can be detected by one or more of branched DNA amplification (BDA), rolling circle amplification (RCA), hybridization signal amplification method (HSAM), ramification amplification method (RAM) and a DNA dendrimer probe. In some aspects, an amplifiable signal element uses a ligand which binds to a second amplifiable signal element. An amplifiable signal element can utilize an enzyme or a catalyst. In some aspects, a detectable signal is amplified prior to detecting the signal corresponding to the replicate nucleic acid.

The invention provides kits to facilitate conducting the methods described herein. For example, a kit can comprise (a) a plurality of chimeric primers each comprising (i) a subsequence comprising a gene specific sequence; (ii) a subsequence comprising a barcode sequence; and (iii) a subsequence comprising a universal priming sequence; and, (b) at least one universal primer that hybridizes to the universal priming sequence. A kit can further comprise a microarray with a set of nucleic acids, wherein each member of the set of nucleic acids is located at a different physical location within the array. Optionally, the gene specific sequences in a kit can hybridize to a polynucleotide sequence in an expressed RNA sample.

The invention also provides methods for the analysis of gene expression, e.g., gene expression profiling. For example, the invention provides a method for determining a gene expression profile with the steps: (a) providing an RNA sample; (b) selectively amplifying a subset of members of the RNA sample by a reverse transcriptase polymerase chain reaction (rtPCR) and generating a set of PCR products, where the rtPCR is performed with a reaction mixture comprising at least one pair of gene-specific primers, which gene specific primers further comprise at least one universal priming sequence; (c) providing an array comprising a set of nucleic acid members corresponding to a plurality of gene expression products, where the nucleic acid members of the set are positioned at discreet physical locations within the array, and where at least one member of the set is complementary to at least a portion of a member of the set of PCR products; (d) hybridizing member PCR products to complementary member nucleic acids of the array; and, (e) detecting a hybridized member PCR product at a discreet physical location in the array, thereby determining a gene expression profile.

The RNA sample used in a method herein can be obtained from a biological sample, e.g., a cell culture or a tissue sample from a patient. In some aspects, the RNA sample includes a control RNA sequence. In some aspects, the RNA sample is amplified using a global amplification of member ribonucleic acids, or alternatively, using a selective amplification of a subset of member ribonucleic acids. In some aspects, the primer comprising at least one universal priming sequence further comprises a detectable moiety, e.g., a fluorescent label, thereby generating a set of detectable PCR products. Alternatively, the universal primer is labeled prior to generating the set of PCR products. In some aspects, the universal primer is labeled after generating the set of PCR products. In some embodiments, the gene-specific primers incorporate at least one barcode sequence. In some aspects, gene-specific primers can further contain a second barcode sequence.

In some embodiments, the amplified RNA sample is a pooled sample of two or more sets of PCR products. In some aspects, an array is a microarray. In some aspects, an array uses a dot blot array. In some aspects, an array comprises an ordered array. In some aspects, the array is a two-dimensional array of nucleic acids, or alternatively, a three-dimensional array of nucleic acids. In some aspects, a competitive hybridization is employed, where a first RNA sample from a first biological source and a second RNA sample from a second biological source are used in the array hybridization. In the competitive hybridization, PCR products generated from the first or the second RNA samples can be labeled, or alternatively, PCR products generated from both RNA samples are labeled. The array-based hybridization and expression profiling can include removing unbound PCR products from the array, e.g., by washing the array with a low stringency buffer.

Optionally, during the amplification steps, at least one primer comprising a universal priming sequence can carry a fluorescence label, where detecting the hybridized PCR product involves determining an intensity of the fluorescence label. Alternatively, a suitably labeled PCR product can be detected by detecting the radiolabel. Optionally, the detection of the hybridized member PCR product is quantitative, where a relative amount of the hybridized member PCR product is determined.

In alternative embodiments for determining a gene expression profile, the invention teaches methods with the following steps: (a) obtaining RNA from one or more biological samples; (b) amplifying the RNA by rtPCR using at least one universal primer and at least one pair of chimeric gene-specific barcoded universal primers, and generating a set of barcoded PCR products; (c) providing an array comprising a set of nucleic acids representing a plurality of gene expression products, wherein members of the set of nucleic acids are positioned at discreet physical locations within the array, and where at least one member nucleic acid is complementary to a barcode sequence of the set of bar coded PCR products; (d) hybridizing members of the set of barcoded PCR products to complementary member nucleic acids of the array; (e) washing the array and removing unbound barcoded PCR products; and (f) detecting and quantitating an amount of barcoded PCR product hybridized to a selected location within the array, thereby determining the gene expression profile.

Variations of this protocol are contemplated. For example, at least one universal primer can be labeled, for example, using a fluorescence label or a radiolabel. In some aspects, the hybridizing step can include at least two sets of barcoded PCR products derived from at least two different biological samples to the array.

The invention also provides kits to facilitate the above method. Such kits can contain various components, for example but not limited to: (a) an array comprising a set of nucleic acids representing a selected set of genes, wherein members of the set of nucleic acids are discreetly located at different physical sites within the array; (b) at least one universal primer; and (c) a plurality of gene-specific primer pairs, wherein member primers comprise a first sequence portion complementary to the universal primer and a second sequence portion complementary to a sequence of a member of the selected set of genes. In some aspects, the set of nucleic acids in the kits representing the selected set of genes comprises a plurality of nucleic acid sequences complementary to portions of the genes. The plurality of gene-specific primer pairs in the kits can further comprise a third bar code sequence portion, where the set of nucleic acids representing the selected set of genes comprises a plurality of nucleic acids complementary to the third bar code sequence portions of the gene-specific primer pairs.

The invention also provides kits for the diagnosis or prognosis of a disease. These kits can contain, for example, (a) an array comprising a set of nucleic acids representing a selected set of genes associated with the disease discreetly located at different physical sites within the array; (b) at least one universal primer; and (c) a plurality of chimeric gene-specific primer pairs having a first sequence portion complementary to the universal primer and a second sequence portion complementary to a sequence of a member of the selected set of genes. The set of nucleic acids representing the selected set of genes in the kit can include a plurality of nucleic acid sequences complementary to portions of the member genes. In these kits, the plurality of gene-specific primer pairs can further comprise a third bar code sequence portion, where the set of nucleic acids representing the selected set of genes comprise a plurality of nucleic acids complementary to the third bar code sequence portions of the gene-specific primer pairs.

DEFINITIONS

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a probe" includes a plurality of identical probe molecules; reference to "cells" includes cells in any form that comprise a plurality of cells, and the like.

Unless otherwise defined, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

"Expression products" are ribonucleic acid (RNA) or polypepetide products transcribed or translated, respectively, from a genome or other genetic element. Commonly, expression products are associated with genes having biological properties. Thus, the term "gene" refers to a nucleic acid sequence associated with biological properties, e.g., encoding a gene product with physiologic properties. A gene optionally includes sequence information required for expression of the gene (e.g., promoters, enhancers, etc.).

The term "gene expression" refers to transcription of a gene into an RNA product, and optionally to translation into one or more polypeptide sequences. The term "transcription" refers to the process of copying a DNA sequence of a gene into an RNA product, generally conducted by a DNA-directed RNA polymerase using DNA as a template.

The term "nucleoside" refers to a compound consisting of a base linked to the C-1' carbon of a sugar, for example, ribose or deoxyribose.

The term "nucleotide" refers generally to a phosphate ester of a nucleoside, as a monomer unit or within a polynucleotide. "Nucleotide 5'-triphosphate" refers to a nucleotide with a triphosphate ester group attached to the sugar 5'-carbon position, and are sometimes denoted as "NTP", or "dNTP" and "ddNTP." A modified nucleotide is any nucleotide (e.g., ATP, TTP, GTP or CTP) that has been chemically modified, typically by modification of the base moiety. Modified nucleotides include, for example but not limited to, methylcytosine, 6-mercaptopurine, 5-fluorouracil, 5-iodo-2'-deoxyuridine and 6-thioguanine. As used herein, the term "nucleotide analog" refers to any nucleotide that is non-naturally occurring.

The terms "nucleic acid," "nucleic acid sequence," "polynucleotide," "polynucleotide sequence," "oligonucleotide," "oligomer," "oligo" or the like, as used herein, refer to a polymer of monomers subunits that can be corresponded to a sequence of nucleotide bases, e.g., a DNA (e.g., cDNA), RNA (e.g., mRNA, rRNA, tRNA, small nuclear RNAs), peptide nucleic acid (PNA), RNA/DNA copolymers, any analogues thereof, or the like. A polynucleotide can be single- or double-stranded, and can be complementary to the sense or antisense strand of a gene sequence. A polynucleotide can hybridize with a complementary portion of a target polynucleotide to form a duplex, which can be a homoduplex or a heteroduplex. The length of a polynucleotide is not limited in any respect. Linkages between nucleotides can be internucleotide-type phosphodiester linkages, or any other type of linkage. A "polynucleotide sequence" refers to the sequence of nucleotide monomers along the polymer. A "polynucleotide" is not limited to any particular length or range of nucleotide sequence, as the term "polynucleotide" encompasses polymeric forms of nucleotides of any length. A polynucleotide can be produced by biological means (e.g., enzymatically), or synthesized using an enzyme-free system. A polynucleotide can be enzymatically extendable or enzymatically non-extendable. Unless otherwise indicated, a particular polynucleotide sequence of the invention optionally encompasses complementary sequences, in addition to the sequence explicitly indicated. Nucleic acid can be obtained from any source, for example, a cellular extract, genomic or extragenomic DNA, viral RNA or DNA, or artificially/chemically synthesized molecules.

Polynucleotides that are formed by 3'-5' phosphodiester linkages are said to have 5'-ends and 3'-ends because the nucleotide monomers that are reacted to make the polynucleotide are joined in such a manner that the 5' phosphate of one mononucleotide pentose ring is attached to the 3' oxygen (hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand. Unless denoted otherwise, whenever a polynucleotide sequence is represented, it will be understood that the nucleotides are in 5' to 3' orientation from left to right.

As used herein, it is not intended that the term "polynucleotides" be limited to naturally occurring polynucleotides sequences or polynucleotide structures, naturally occurring backbones or naturally occurring internucleotide linkages. One familiar with the art knows well the wide variety of polynucleotide analogues, unnatural nucleotides, non-natural phosphodiester bond linkages and internucleotide analogs that find use with the invention. Non-limiting examples of such unnatural structures include non-ribose sugar backbones, 3'-5' and 2'-5' phosphodiester linkages, internucleotide inverted linkages (e.g., 3'-3' and 5'-5'), branched structures, and internucleotide analogs (e.g., peptide nucleic acids (PNAs), locked nucleic acids (LNAs), $C_1$-$C_4$ alkylphosphonate linkages such as methylphosphonate, phosphoramidate, $C_1$-$C_6$ alkyl-phosphotriester, phosphorothioate and phosphorodithioate internucleotide linkages. Furthermore, a polynucleotide can be composed entirely of a single type of monomeric subunit and one type of linkage, or can be composed of mixtures or combinations of different types of subunits and different types of linkages (a polynucleotide can be a chimeric molecule). As used herein, a polynucleotide analog retains the essential nature of natural polynucleotides in that they hybridize to a single-stranded nucleic acid target in a manner similar to naturally occurring polynucleotides.

The term "RNA," an acronym for ribonucleic acid, refers to any polymer of ribonucleotides. The term "RNA" can refer to polymers comprising natural, unnatural or modified ribonucleotides, or any combinations thereof (i.e., chimeric RNA molecules). The term "RNA" includes all biological forms of RNA, including for example, mRNA (typically polyA RNA), rRNA, tRNA, and small nuclear RNAs, as well as non-naturally occurring forms of RNA, including cRNA, antisense RNA, and any type of artificial (e.g., recombinant) transcript not endogenous to a cellular system. The term RNA also encompasses RNA molecules that comprise non-natural ribonucleotide analogues, such as 2-O-methylated ribonucleotides. RNA can be produced by any method, including by enzymatic synthesis or by artificial (chemical) synthesis. Enzymatic synthesis can include cell-free in vitro transcription systems and cellular systems, e.g., in a prokaryotic cell or in a eukaryotic cell.

The term "cDNA" refers to complementary or "copy" DNA. Generally cDNA is synthesized by a DNA polymerase having reverse transcriptase activity (e.g., a nucleic acid polymerase that uses an RNA template to generate a complementary DNA molecule) using any type of RNA molecule (e.g., typically mRNA) as a template. Alternatively, the cDNA can be obtained by directed chemical syntheses.

The terms "amplification," "amplified product" or "amplified nucleic acid" refer to a nucleic acid generated by any method of nucleic acid amplification. In some aspects, "amplified" generally refers to an increase in the absolute concentration of a component nucleic acid in a mixture. In other aspects, the term "amplified" refers to an enrichment of a nucleic acid component in a mixture relative other nucleic acids in the mixture (with or without an increase in the absolute concentration of the nucleic acid of interest). As used herein, the process of amplification of a nucleic acid includes processes that can result in the amplified product having a different chemical structure but retaining the primary base (nucleotide) sequence corresponding to the original nucleic acid. For example, as used herein, an amplified mRNA can include cDNA molecules, wherein the cDNA molecules retain at least a portion of the primary base sequence of the original mRNA. In some embodiments, amplification is optionally followed by additional steps, for example, but not limited to, labeling, sequencing, purification, isolation, hybridization, size resolution, expression, detecting and/or cloning.

The terms "complementary" or "complementarity" refer to nucleic acid sequences capable of base-pairing according to the standard Watson-Crick complementary rules, or being capable of hybridizing to a particular nucleic acid segment under relatively stringent conditions. Optionally, nucleic acid polymers are optionally complementary across only portions of their entire sequences. As used herein, the terms "complementary" or are used in reference to antiparallel strands of polynucleotides related by the Watson-Crick (and optionally Hoogsteen-type) base-pairing rules. For example, the sequence 5'-AGTTC-3' is complementary to the sequence 5'-GAACT-3'. The terms "completely complementary" or "100% complementary" and the like refer to complementary sequences that have perfect Watson-Crick pairing of bases between the antiparallel strands (no mismatches in the polynucleotide duplex). The terms "partial complementarity," "partially complementary," "incomplete complementarity" or "incompletely complementary"and the like refer to any alignment of bases between antiparallel polynucleotide strands that is less than 100% perfect (e.g., there exists at least one mismatch in the polynucleotide duplex). Furthermore, two sequences are said to be complementary over a portion of their length if there exist one or more mismatch, gap or insertion in their alignment.

The term "hybridization" refers to duplex formation between two or more polynucleotides, e.g., to form a double-stranded nucleic acid. The ability of two regions of complementarity to hybridize and remain together depends of the length and continuity of the complementary regions, and the stringency of hybridization conditions. In describing hybridization between any two nucleic acids (e.g., between an array probe and an amplified RNA target such as a cDNA), sometimes the hybridization encompasses "at least a portion" of the target or probe. As used herein, the phrase "at least a portion" and similar phrases in reference to hybridization reactions refer to a domain of complementarity that is sufficiently large to permit sequence-specific hybridization, e.g., allows stable duplex formation under stringent hybridization conditions.

A "defined sequence probe" is a nucleic acid probe having a single polynucleotide sequence. The term "synthetic probe" is used to indicate that the probe is produced by one or more synthetic or artificial manipulations, e.g., by chemical oligonucleotide synthesis, restriction digestion, amplification, cDNA synthesis, and the like.

The term "label" refers to any detectable moiety, or a moiety that permits detection but is not by itself detectable. A label can be used to distinguish a particular nucleic acid from others that are unlabeled, or labeled differently, or the label may be used to enhance detection.

The term "primer" refers to any nucleic acid that is capable of hybridizing at least at its 3' end to a complementary or partially complementary nucleic acid molecule, where the free 3' hydroxyl terminus is capable of being extended by a nucleic acid polymerase in a template-dependent manner.

The term "template" refers to any nucleic acid polymer that can serve as a sequence that can be copied into a complementary sequence by the action of, for example, a polymerase enzyme.

The term "target," "target sequence," or "target gene sequence" refers to a specific nucleic acid sequence (or a homologous variant of that sequence), the presence, absence or abundance of which is to be determined. In a preferred embodiment of the invention, it is a unique sequence within the mRNA of an expressed gene.

The term "target-specific primer" refers to a primer capable of hybridizing with its corresponding target sequence, to the exclusion of other non-target sequences. Under appropriate conditions, the hybridized primer can prime the replication of the target sequence.

The term "semi-universal primer" refers to a primer that is capable of hybridizing with more than one (e.g., a subset), but not all, of the potential target sequences in a multiplexed reaction. The term "universal primer" refers to a replication primer comprising a universal sequence.

The terms "universal sequence," "universal priming sequence" or "universal primer sequence" or the like refer to a sequence contained in a plurality of primers, but preferably not in a complement to the original template nucleic acid (e.g., the target sequence), such that a primer composed entirely of universal sequence (i.e., a universal primer) is not capable of hybridizing with the template.

The term "reference sequence" refers to a nucleic acid sequence serving as a target of amplification in a sample that provides a control for the assay. The reference may be internal (or endogenous) to the sample source, or it may be an externally added (or exogenous) to the sample. An external reference may be either RNA, added to the sample prior to reverse transcription, or DNA (e.g., cDNA), added prior to PCR amplification.

The term "multiplex reaction" refers to a plurality of reactions conducted simultaneously in a single reaction mixture, and includes, for example, multiplex amplification and multiplex hybridization reactions.

The term "multiplex amplification" refers to a plurality of amplification reactions conducted simultaneously in a single reaction mixture.

In the context of the present invention, the term "simultaneously" means that more than one reaction (e.g., a plurality of hybridization reactions) occur at substantially the same time. For example, reagents to be hybridized, such as multiple defined sequence probes are contacted at the same time and/or in the same solution with target nucleic acids, e.g., an array of nucleic acids.

In the context of the present invention, an "amplifiable signal element" is a component of a probe that facilitates amplification of a signal following hybridization of the probe to a target sequence.

The term "gene expression data" refers to one or more sets of data that contain information regarding different aspects of gene expression. The data set optionally includes information regarding: the presence of target-transcripts in cell or cell-derived samples; the relative and absolute abunda ability of various treatments to induce expression of specific genes; and the ability of various treatments to change expression of specific genes to different levels.

The term "quantitating" means to assign a numerical value, e.g., to a hybridization signal. Typically, quantitating involves measuring the intensity of a signal and assigning a corresponding value on a linear or exponential numerical scale.

The term "relative abundance" or "relative gene expression levels" refers to the abundance of a given species relative to that of a second species. Optionally, the second species is a reference sequence.

The term "treatment" refers to the process of subjecting (i.e., treating) one or more cells, cell lines, tissues, or organisms to a condition, substance, or agent (or combinations thereof) that may cause the cell, cell line, tissue or organism to alter its gene expression profile. A treatment may include a range of chemical concentrations and exposure times, and replicate samples may be generated. The term "chemical treatment" refers to the process of exposing (or contacting) a cell, cell line, tissue or organism to (or with) a chemical or biochemical compound (or library of compounds) that has/have the potential to alter its gene expression profile.

The term "platform" refers to the instrumentation method used for sample preparation, amplification, product separation, product detection, or analysis of data obtained from samples.

The terms "microplate," "culture plate," and "multiwell plate" interchangeably refer to a surface having multiple chambers, receptacles or containers and generally used to perform a large number of discreet reactions simultaneously.

The term "high throughput format" refers generally to a relatively rapid completion of an analysis. In one aspect, the term "high throughput" refers to the highly parallel analysis of many samples (e.g., the simultaneous analysis of many samples). In another aspect, "high throughput analysis" refers to completing an analysis of more than about 10 samples per hour, preferably about 50 or more samples per hour, more preferably about 100 or more samples per hour, most preferably about 250, about 500, about 1000 or more samples per hour.

The term "miniaturized format" refers to procedures or methods conducted at submicroliter volumes, including on both microfluidic and nanofluidic platforms.

BRIEF DESCRIPTION OF THE FIGURES

FIG. 5A provides a diagram illustrating use of a soluble secondary labeled probe. In this figure, an amplified gene or other nucleic acid product, e.g., a cDNA PCR product, comprises two barcode sequences. One barcode (Barcode A) hybridizes to a complementary barcode probe attached to the array surface (i.e., a specific generic probe at a specific spatial position within a generic array), and the second barcode (Barcode B) hybridizes to a generic soluble oligonucleotide probe carrying a label.

FIG. 5B provides a diagram illustrating use of a soluble secondary labeled probe in conjunction with a soluble linking oligomer in the barcode microarray. In this figure, an amplified gene or other nucleic acid product, e.g., a cDNA PCR product, comprises only one barcode sequence (Barcode A). The one barcode on the PCR product (Barcode A) hybridizes to a complementary barcode probe attached to the array surface (i.e., a specific generic probe at a specific spatial position within a generic array). A linking oligonucleotide is added to the hybridization reaction, where the linking oligo comprises gene-specific sequence complementary to the amplified product and further comprises a barcode sequence (Barcode B) that is different from the first barcode sequence. A generic soluble Barcode B-specific labeled probe is then hybridized to the linking oligo, thereby permitting detection of the amplified product.

FIG. 6 provides a diagram illustrating use of sample-specific barcode sequences, arrays comprising sample-specific barcode sequence probes (i.e., attachment moieties) and secondary soluble gene-specific labeled probes using a plurality of labels for the selective localization and detection of amplified nucleic acids from multiple samples.

FIG. 7 provides a diagram illustrating use of gene-specific barcode sequences, arrays comprising gene sequence attachment moieties, and secondary soluble barcode-specific labeled probes for the selective localization and detection of amplified nucleic acids from multiple samples.

FIG. 8 provides a diagram illustrating the use of simultaneously incorporated gene-specific and sample-specific barcode sequences, arrays comprising sample-specific sequence attachment moieties and secondary soluble labeled barcode probes for the selective localization and detection of amplified nucleic acids from multiple samples.

FIG. 9 provides a diagram illustrating the use of sample-specific barcode sequences, arrays comprising barcode sequence attachment moieties, linker oligonucleotides comprising gene-specific and barcode probe specific sequences, and secondary soluble labeled barcode probes for the selective localization and detection of amplified nucleic acids from multiple samples.

FIG. 10 provides a diagram illustrating the use of simultaneously incorporated gene-specific and sample-specific barcode sequences, arrays comprising barcode sequence attachment moieties, linker oligonucleotides comprising gene-specific barcodes and probe barcode sequences, and secondary soluble labeled barcode probes for the selective localization and detection of amplified nucleic acids from multiple samples.

DETAILED DESCRIPTION OF THE INVENTION

Novel Methods for Expression Profiling using Microarray Analysis

Described herein are methods that overcome the principal problems of cost and sensitivity associated with preparing samples for microarray analysis. In a typical embodiment, the described invention makes use of reverse transcription coupled polymerase chain reaction (rtPCR) to amplify a selected set of RNA transcripts, e.g., from a biological sample. A detectable moiety (such as a fluorescent label), suitable for microarray analysis, is incorporated during the amplification reaction, converting the amplification and labeling into a simple one-step process, in contrast to most current amplification methods.

It has previously been demonstrated that PCR and rtPCR can be used to amplify a multiplex of targets using very small amounts of material. This advantage has been utilized for a variety of applications including genotyping and gene expression. In many cases, especially gene expression, it is desirable to quantitate the relative expression levels for the different nucleic acid targets. However, standard multiplex rtPCR is not typically quantitative. Significant biases can be introduced during the exponential amplification that results in variable and nonreproducible data. These biases result from primer-primer interactions, primer-product cross-reactions, and from concentration and sequence-dependent variations in amplification efficiency, most notably seen in the latter part or plateau phase of thermal cycling. To overcome these deficiencies, methods of the invention employ a modified rtPCR process that universal primers to drive sequence amplification.

Figure 1:
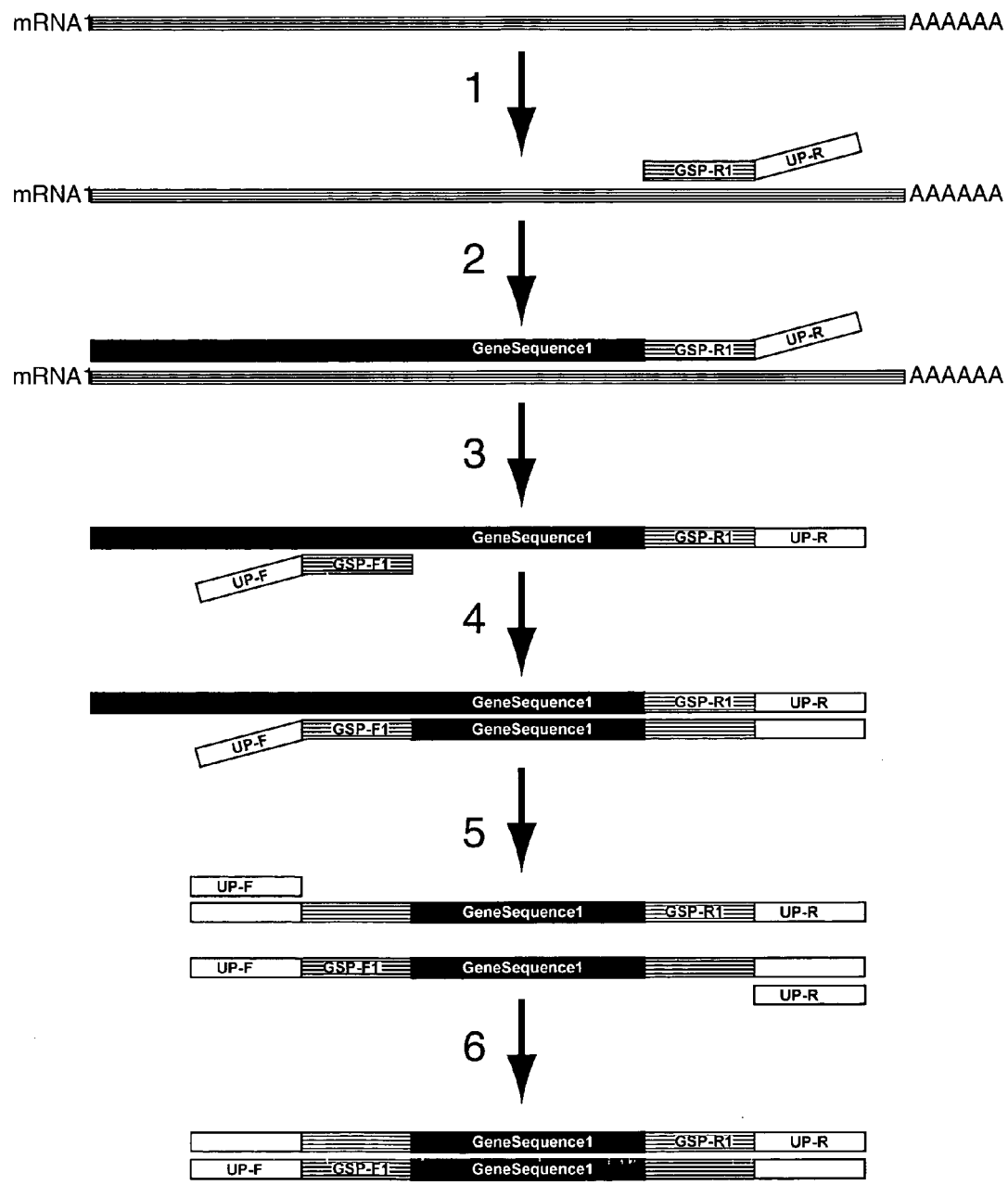
FIG. 1 provides a schematic illustration of the universal primer UP-rtPCR process for a single RNA transcript, mRNA1, within the RNA pool. Step 1, the chimeric reverse gene-specific, universal primer (GSP-R1_UP-R) is hybridized to the mRNA1 transcript. Step 2, the GSP-R1_UP-R primer is extended by reverse transcriptase, generating a cDNA product. Step 3, following denaturation, the chimeric forward gene-specific, universal primer (GSP-F1_UP-F) hybridizes to the cDNA complement. Step 4, the GSP-F1_UP-F primer is extended by DNA polymerase producing a complementary strand to the cDNA and incorporates the UP-R sequence on the end. This sequence can now act as a template for the reverse universal primer (UP-R). Step 5, following an additional cycle of denaturing, hybridization and polymerization the UP-rtPCR reaction generates PCR products that are tailed at both ends by the universal primer sequence. These strand can then denature and provide templates for the hybridization of both the forward and reverse universal primers (UP-F and UP-R, respectively). Step 6, as the thermal cycling continues the predominant product is the universal-primer-tailed, double-stranded PCR product.
Figure 2:
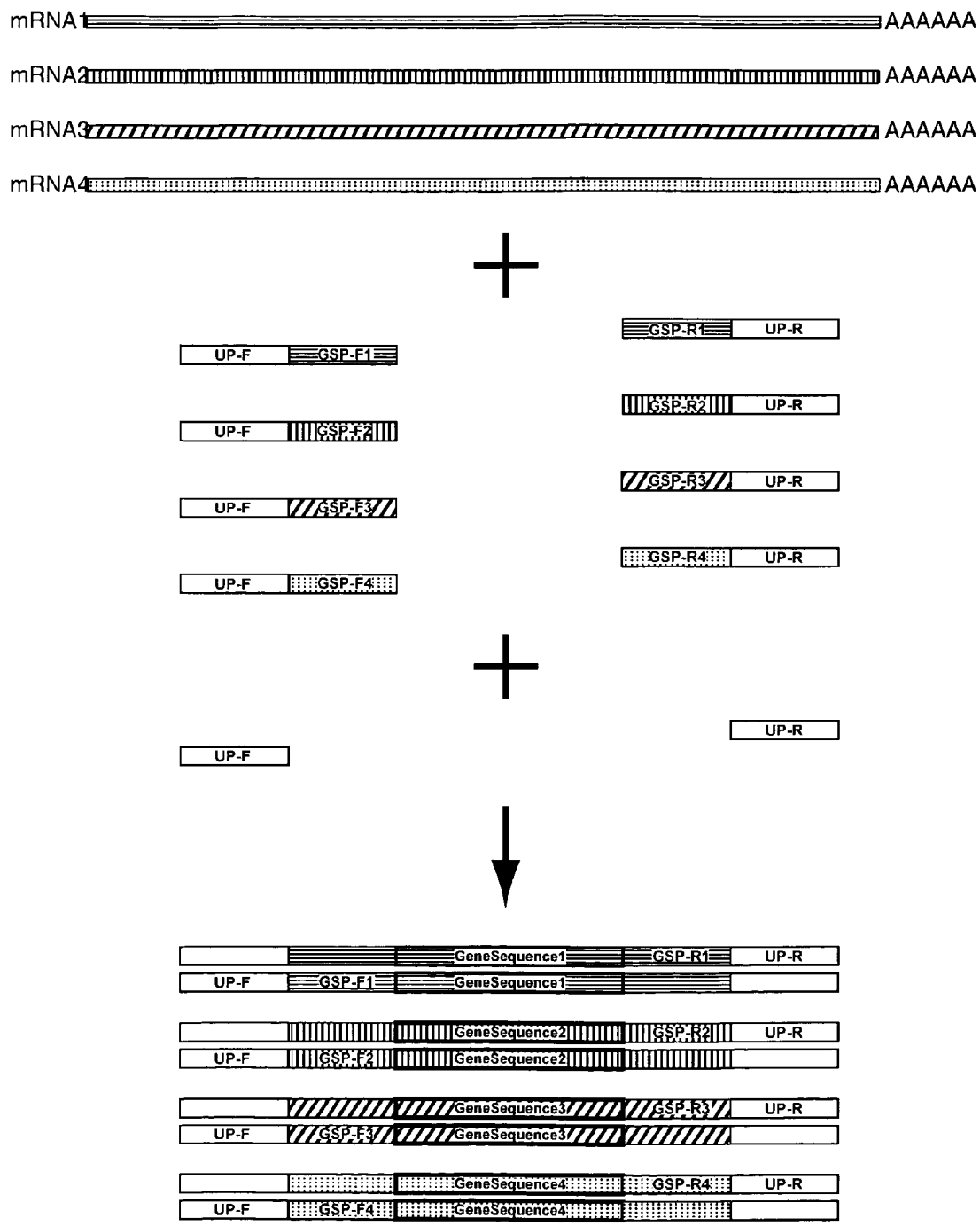
FIG. 2 provides a schematic illustration of the specific nucleic acid reagents in a UP-rtPCR multiplex reaction with four different mRNA targets (mRNA 1, mRNA2, mRNA3 and mRNA4). Added to the mRNAs are the set of four different chimeric gene-specific, universal primer pairs (GSP-F1_UP-F & GSP-R1_UP-R; GSP-F2_UP-F & GSP-R2_UP-R; GSP-F3_UP-F & GSP-R3_UP-R; and GSP-F4_UP-F & GSP-R4_UP-R), and the pair of universal primers (UP-F & UP-R). This mixture of primers and mRNAs generates four different PCR products each tailed with the universal primer sequences.

The modified rtPCR process uses a combined gene-specific, universal priming strategy that overcomes the primary deficiencies of rtPCR without compromising the detection sensitivity that is gained using this process. The strategy is outlined in FIGS. 1 and 2. The process involves the conversion of a multiplex amplification process from one involving tens of primers to a process utilizing only two primers (i.e., universal primers). The reaction initializes using gene-specific primers (Gene Specific Primer-Forward (GSP-F) and Gene Specific Primer-Reverse (GSP-R)) that are capable of hybridizing to sequences in each target mRNA. These gene-specific primers carry on their 5' ends a consensus or universal priming sequence (Universal Primer-Forward (UP-F) and Universal Primer Reverse (UP-R)). During the first few cycles of amplification the specific gene targets are amplified by these chimeric primers, creating products that are tailed with the universal primer sequence. Subsequent amplification typically results from extension of universal primers which hybridize to the complement of the universal priming sequence.

In certain embodiments, the reactions carry a pair of universal primers present at higher concentrations than the chimeric-gene-specific primers. For example, in one embodiment a universal:chimeric gene-specific primer ratio of 50:1 is used (1 µM universal:0.02 µM gene specific). In another embodiment the ratio is between 10:1 and 100:1. Therefore, as PCR progresses the amplification is quickly taken over by the single pair of universal primers. This transition from the use of many primers to only two effectively collapses the level of reaction complexity and locks in the relative concentrations of the different gene targets. In the universal primer amplification reaction all the products are effectively the same chemical species and are not differentially amplified. There are some potential limitations in terms of the size range of PCR products, for example in one preferred embodiment all of the PCR products are less than 400 base pairs in length, but the relative gene ratios can be maintained even as the reaction pushes into the plateau phase.

The universal-primer rtPCR (UP-rtPCR) method has been demonstrated to work and generate PCR products that have been analyzed by electrophoretic methods, ABI capillary and slab instruments, as described in detail in U.S. Pat. No. 6,618,679 to Loehrlein et al., entitled "METHODS FOR ANALYSIS OF GENE EXPRESSION." Following amplification, the products can be differentiated and quantitated by electrophoresis because each gene has been designed to generate a different size PCR product. This size differentiation involves the resolution of each distinct product in the electrophoretic process in order to quantitate the product via measurement of peak height and/or peak area. Typically only a limited number of products can be amplified and detected in a single electrophoretic run. Methods of the invention extend the multiplexed UP-rtPCR technology to significantly increased numbers of different genes by incorporating the use of microarray analysis.

Microarray analysis for expression profiling involves typically the use of a series of nucleic acid probes arrayed in a one-, two- or even three-dimensional format on a surface, wherein each of the probes is has a unique location or address on the surface. The nucleic acid probes (including, for example but not limited to, oligonucleotides, PCR products, cDNA, plasmids or nucleic-acid-like synthetic polymers, all of which are capable of sequence specific hybridization) are made to be complementary to the sequences of the genes to be analyzed. The number of distinct probes that can be spotted to unique addressable locations on a single microarray is upwards of tens of thousands, and is constantly being revised upwards with improving state-of-the-art technology. The number of genes of interest to an investigator, and indeed the total number of expressed genes in any one RNA sample, is likely to be smaller than the probe capacity on a state-of-the-art microarray; thus, the number of probes required for any one analysis is likely to be well within the upper limit of microarray probe capacity. In some embodiments, the described method is used to amplify 10 to 1000 different RNA transcripts. Commonly, the described method is used to amplify 20 to 500 different RNA transcripts, e.g., between 50 and 200 different RNA transcripts.

UP-rtPCR Versus Current Microarray Amplification and Labeling Methods

In a standard microarray protocol, the mRNA population is converted to cDNA by reverse transcription and globally labeled, e.g., with a fluorescent dye such as cy3 or cy5. The labeling step is either performed as part of the reverse transcription reaction, using a dye-labeled dNTP, or post reverse transcription using a chemically activated dye that couples to amino-dUTP incorporated during the reverse transcription step. The labeled product is then purified away from unincorporated dye and then placed on the array and the different gene sequences are allowed to hybridize to their complementary probes. The standard protocol requires a large amount of RNA, e.g. 100 µg to 1 mg of total RNA, for starting material. In order to use less RNA starting material, the additional step of global amplification is frequently performed. Examples of global amplification methods include the SMART™ technology from BD Biosciences-Clontech (Palo Alto, Calif.), Ovation™ amplification technology from NuGEN™ Technologies, Inc. (San Carlos, Calif.), and RiboAmp™ RNA Amplification kit from Arcturus, Inc. (Mountain View, Calif.). The global amplification step adds additional cost to the method. For example, the list price on global amplification methods capable of amplifying from tens of ng of total RNA ranges from $100 to $200 per sample. This cost is in addition to the $50-$100 in labeling reagents used per sample. In contrast, the reagent costs for the performance of a UP-rtPCR reaction is between $1 and $3 per sample.

Thus, the methods described herein coupling UP-rtPCR with microarray analysis offer several distinct advantages over current microarray sample preparation methods. These advantages include (1) being able to use very small amounts of total RNA per sample, (2) single step cDNA conversion, amplification and labeling, (3) selective amplification of only those genes targeted for analysis, and (4) reduced labor and reagent costs because of the process simplicity.

Working with small amounts of RNA is very valuable in a number of research and clinical settings. By being able to use very small amounts of total RNA per sample, e.g. 10 ng or less, the UP-rtPCR method can be applied to the analysis of small clinical samples. For example, needle biopsies to scan for cancer or to monitor the health of an organ or tissue typically extract only very small numbers of cells, that yield only tens of nanograms of total RNA, far too little for standard microarray analysis.

Similarly, high throughput screening of chemical libraries involves the treatment of cells grown in cell culture with a plurality of compounds. These treatments are routinely performed in microtiter-plate format. It is highly desired in these screens to reduce cost per assay by using high density microtiter plates, e.g., 96-well, 384-well and 1536-well plates. Performance in the higher density, lower volume plates means that less of each compound is used per treatment, which is advantageous since some compounds may be in very limited supply and/or be expensive to synthesize or otherwise obtain. Using smaller cell cultures also means that fewer cells are present, which will yield only nanograms of total RNA available for expression analysis.

Single step cDNA conversion, amplification and labeling that is possible with UP-rtPCR creates a fundamentally simpler process than existing methods. Even the Ovation method developed by Nugen, which represents one of the simplest approaches to amplification and labeling for microarray analysis, involves multiple independent steps for amplification, purification and labeling.

The utilization of UP-rtPCR for targeted gene amplification provides improvements both for the large gain in sensitivity and because it reduces the complexity of the sample to be analyzed on the array. The use of targeted amplification of a small set of gene versus one of the global RNA amplification methods ensures the maximum level of discrimination, limiting cross hybridization of the different probes to one or more amplified homologous or partially homologous genes. And because the amplification is focused on only the small set of genes, all of the label is incorporated in only those genes to be analyzed, leading to a potentially significant increase in signal-to-noise ratio for those genes versus global methods.

Process simplicity leads to reduced costs of performance. The minimal steps in amplification and labeling using the UP-rtPCR process leads to reduced time and labor associated with preparing the samples for each of the different steps. The elimination of two-step labeling chemistries reduces the reagent costs. In the UP-rtPCR process all of the label is carried on one or both universal primers requiring only one labeling synthesis that can be used for 10,000 or more samples. The choice of a variety of standard, off-the-shelf rtPCR reagents from multiple vendors for use in the rtPCR process also means reagent costs will be low.

The UP-rtPCR process is amenable to a number of different approaches for microarray analysis. These approaches include, (i) single-sample, single-color hybridization; (ii) two-color, two-sample competitive hybridization, as well as (iii) a plurality of samples/colors competitive hybridizations. When conducting concurrent (i.e., parallel) analysis of a plurality of samples (e.g., more than two original sources of RNA), the upper limit of the number of samples that can be analyzed in generally limited by the types of detectable moieties used (e.g., labels) and the detection system, and is not limited by the UP-rtPCR process.

For example, typical radiolabel-based detection systems are limited to one label, while fluorescence-based systems routinely use two labels, and with some systems incorporating as many as five labels. One skilled in the art can utilize any of a variety of different labeling and detection schemes in the context of UP-rtPCR and microarray analysis, including but not limited to calorimetric, chemiluminescent, surface plasmon resonance, and combination label systems including the use of photon emission and quenching systems. In some embodiments, the detectable moiety is linked to one or both universal primers used in the UP-rtPCR process.

Introduction of "Barcode" Sequences.

Figure 3:
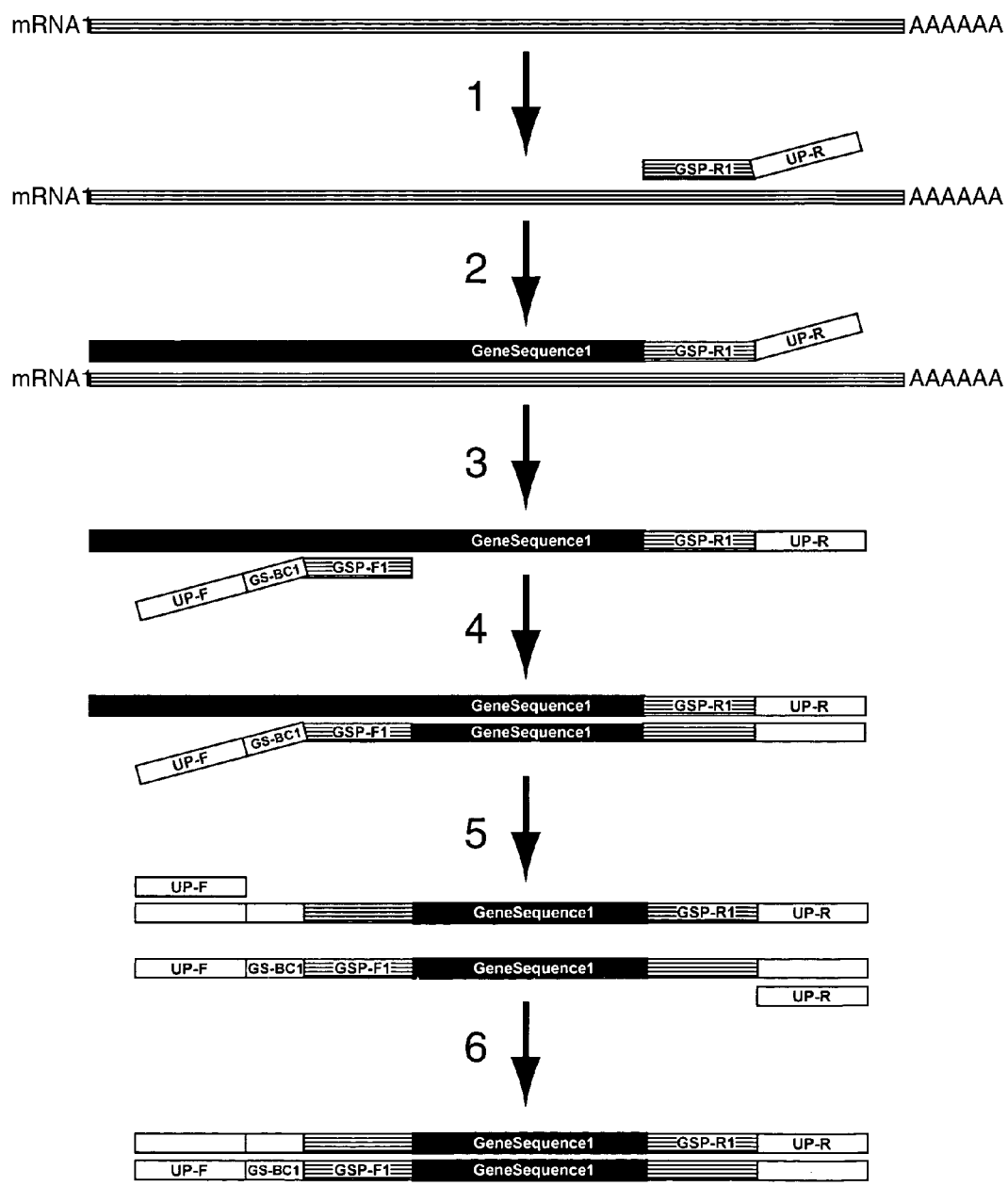
FIG. 3 provides a schematic illustration of the process as described in FIG. 1, except with a modification of the GSP-F1_UP-F to incorporate a gene-specific barcode sequence, GS-BC1. The GS-BC1 sequence is consequently incorporated into the final PCR product set and may be used for hybridization to the microarray.
Figure 4:
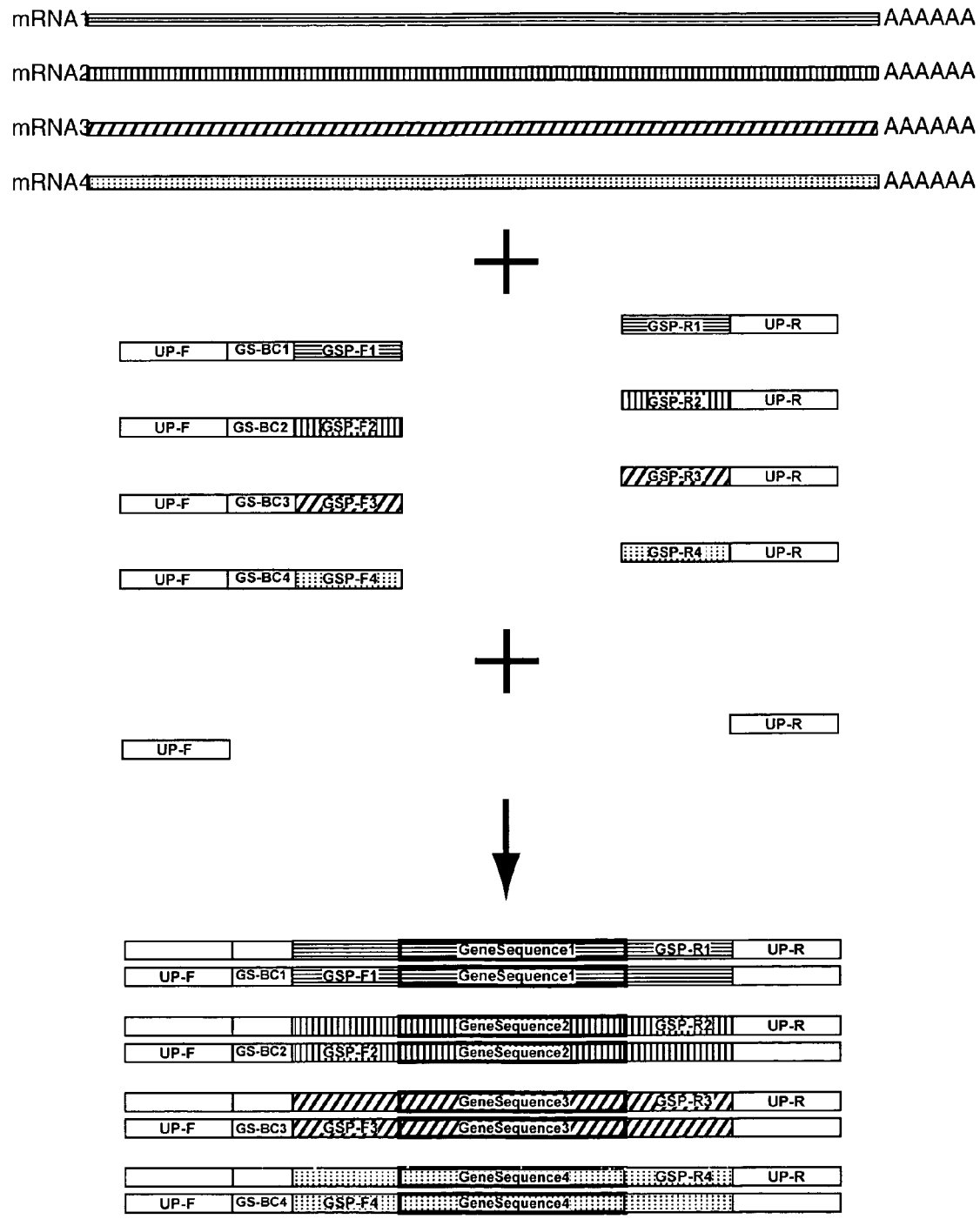
FIG. 4 provides a schematic illustration of the nucleic acid ingredients and described in FIG. 2, except with a modification of the GSP-F_UP-F primers to incorporate a gene-specific barcode sequence, GS-BC, for each of the 4 different mRNA target sequences (GS-BC1, GS-BC2, GC-BC3, and GS-BC4). The GS-BC sequences are consequently incorporated into the final PCR product set and may be used for hybridization to the microarray.

Other embodiments of the UP-rtPCR process involve the modification of the chimeric gene-specific primers to include an additional nucleic acid "barcode" sequence that can be incorporated during the UP-rtPCR process. In such an embodiment each of the genes to be amplified is linked to a barcode sequence. A barcode sequence added to a sample can be sample specific (e.g., where multiple samples are analyzed concurrently) or in a gene specific manner, where each gene receives a different barcode. Alternatively still, any particular subset of genes can receive the same barcode during the UP-rtPCR process. Various embodiments utilizing the barcode strategy for sample or gene differentiation are illustrated in FIGS. 3 and 4. The embodiments illustrated in the figures herein are intended to serve only as examples; it is not intended that the invention be limited to any particular barcode scheme illustrated herein. After reading a description of the invention, a variety of embodiments will be apparent to one of skill in the art, all of which are encompassed by the scope of the claimed invention.

In some embodiments, an amplification process is used to produce a plurality of different nucleic acid sequences, e.g. corresponding to RNA transcripts. Through the use of different chimeric primer sequences, it is possible to incorporate barcode sequences into the amplified products. The types of barcodes incorporated and the populations that contain a barcode vary depending upon the sequence composition of the different oligonucleotide primers used. For example, the use of PCR involves the use of a pair of oligonucleotide primers for each gene or nucleic acid region to be amplified. Because each gene is linked to its own pair of oligonucleotide primers it is possible to uniquely select the barcode sequences that will be associated with each gene. It is therefore possible to incorporate barcodes that fall into one of three different categories. The categories are (a) where each different amplified gene or nucleic acid region has a unique bar code, (b) where two or more different amplified gene or nucleic acid regions comprising a group may share a barcode with one or more barcodes associated with different groups, or (c) where all of the different amplified gene or nucleic acid regions possess the same barcode. There is also the option to include more than one barcode per amplified product and therefore associate bar codes from one or more of the above list categories simultaneously. In one embodiment of the invention the universal primer or semi-universal primer can also function as the bar code sequence falling under categories (b) and (c).

In one embodiment, the Gene-Specific Barcode (GS-BC) sequence is incorporated within the chimeric universal/gene specific primer. Specifically the gene specific codes are place in between the universal primer (UP) sequence and the gene specific primer (GSP) sequence. For example, in FIGS. 3 and 4 the GS-BC sequences are incorporated into the forward primers. The GS-BC sequences are then incorporated into all amplified products.

Alternative, non-limiting embodiments of the invention employing the incorporation of one or more barcode sequences into nucleic acids corresponding to expressed RNA samples are illustrated schematically in FIGS. 6 through 10.

Figure 6:
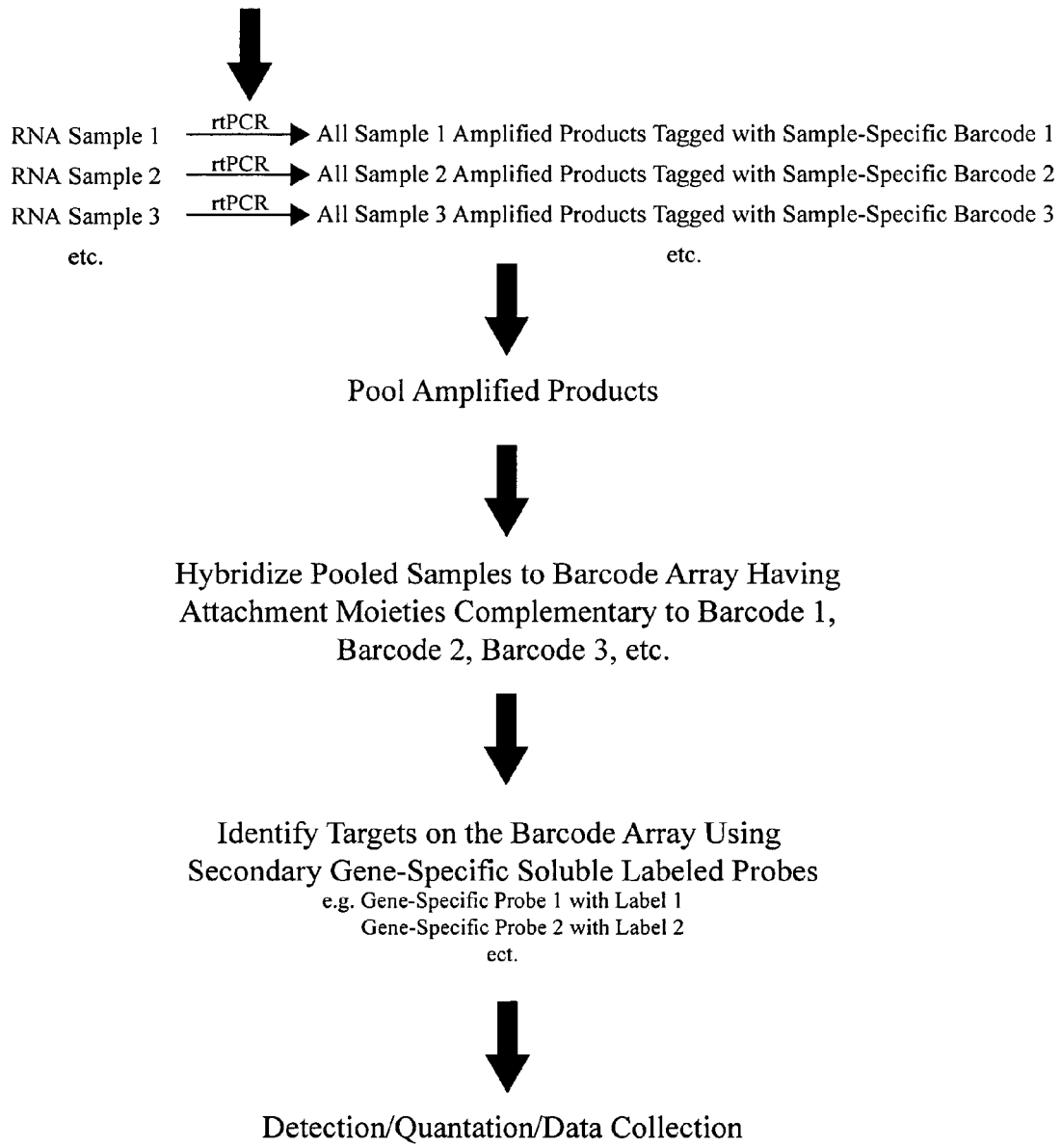
FIG. 6 through FIG. 10 provide diagrams illustrating various, non-limiting embodiments of the invention.

FIG. 6 illustrates a microarray-based expression profiling scheme using sample-specific barcodes. RNA from various samples is reverse transcribed and amplified. This amplification will typically, but not exclusively, use gene-specific primers, although global RNA amplification is also possible. The amplification is designed to use primers that will simultaneously incorporate a barcode into all the amplified products from each sample (i.e., in a sample-specific manner; the barcode for sample 1 is different from the barcode for sample 2, which is again different from the barcode for sample 3, etc.).

Following amplification, the amplified products can be pooled and applied to a suitable array. In one embodiment (pictured in FIG. 6), the array comprises stationary probes (i.e., attachment moieties) specific for (i.e., complementary to) the various sample barcodes. Such an array configuration can be considered a generic array. The resulting hybridization complexes can then be visualized using labeled, soluble (i.e., not affixed) gene-specific probes. Alternatively, the array can use gene-specific capture probes, and the resulting hybridization complexes can be detected using labeled soluble probes complementary to the sample-specific barcodes. Practical applications of this method (and other methods as described in FIGS. 6 through 10) will likely use arrays of arrays to maximize through-put. Similarly, in all of these methods, each labeled soluble visualization probe can labeled with a different moiety that permits differentiation of different hybridization complexes (i.e., each probe is coupled to a label that has a unique excitation/emission spectra relative to the other labels on the other probes). This type of labeling strategy allows highly parallel processing of numerous samples and numerous genes.

Figure 7:
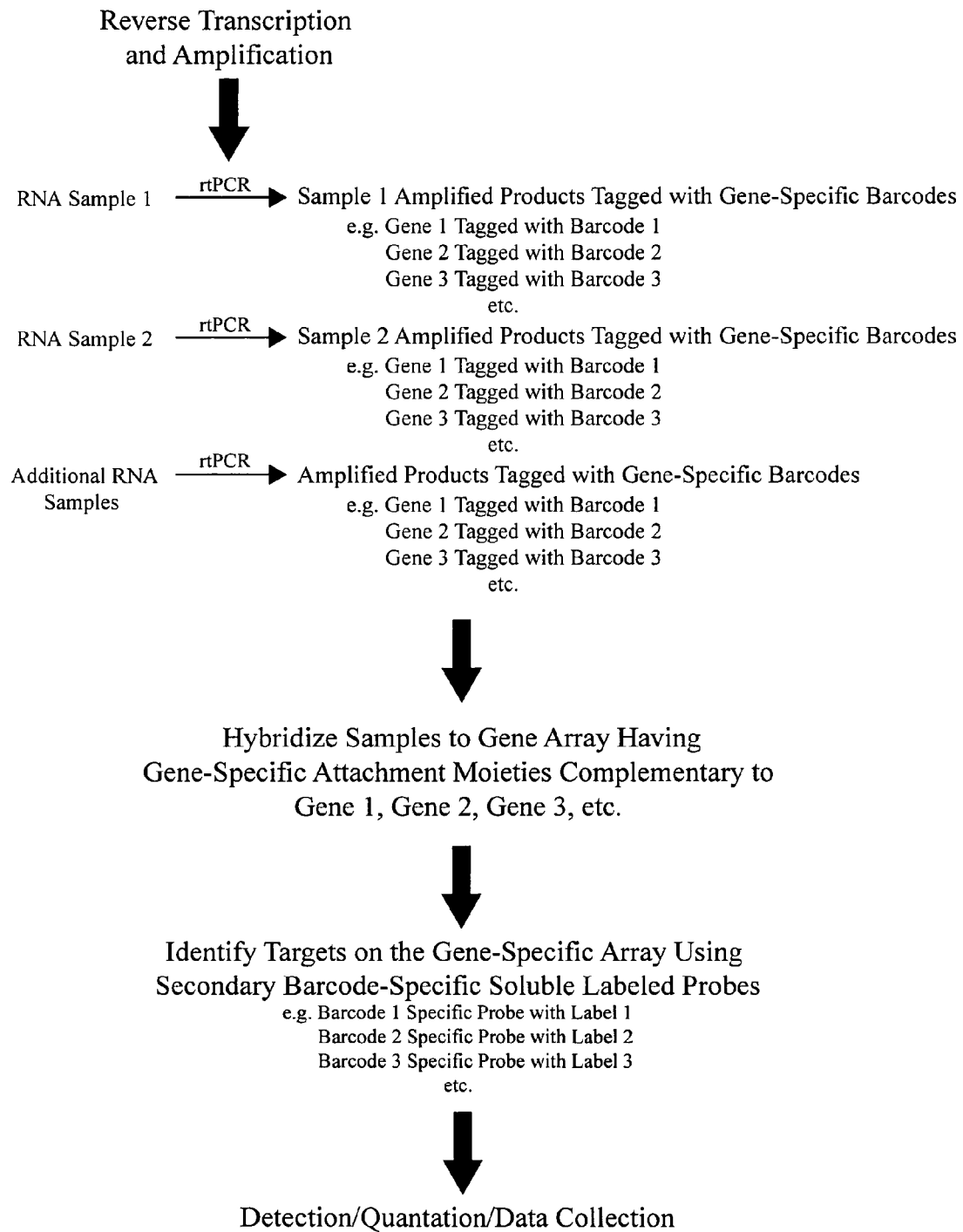

FIG. 7 illustrates a microarray-based expression profiling scheme using gene-specific barcodes. RNA from various samples is selectively reverse transcribed and amplified using gene specific primers, simultaneously incorporating a barcode in a gene-specific manner, i.e., the gene-1 amplicon contains barcode-1, the gene-2 amplicon contains barcode-2, etc. When RNA samples from multiple sources are amplified, the target gene amplicons receive the same barcode across samples. This situation is analogous to FIGS. 3 and 4 (except these figures only show the amplification products for a single transcript (FIG. 3) and from a single sample (FIG. 4).

Following selective amplification, the amplified products are applied to a suitable array. In one embodiment (pictured in FIG. 7), the array comprises stationary probes (i.e., attachment moieties) specific for (i.e., complementary to) the various gene-sequences. The resulting hybridization complexes can then be visualized using labeled, soluble (i.e., not affixed)

barcode visualization probes. Alternatively, the array can use barcode-specific capture probes, and the resulting hybridization complexes can be detected using labeled soluble probes complementary to specific gene sequences.

Figure 8:
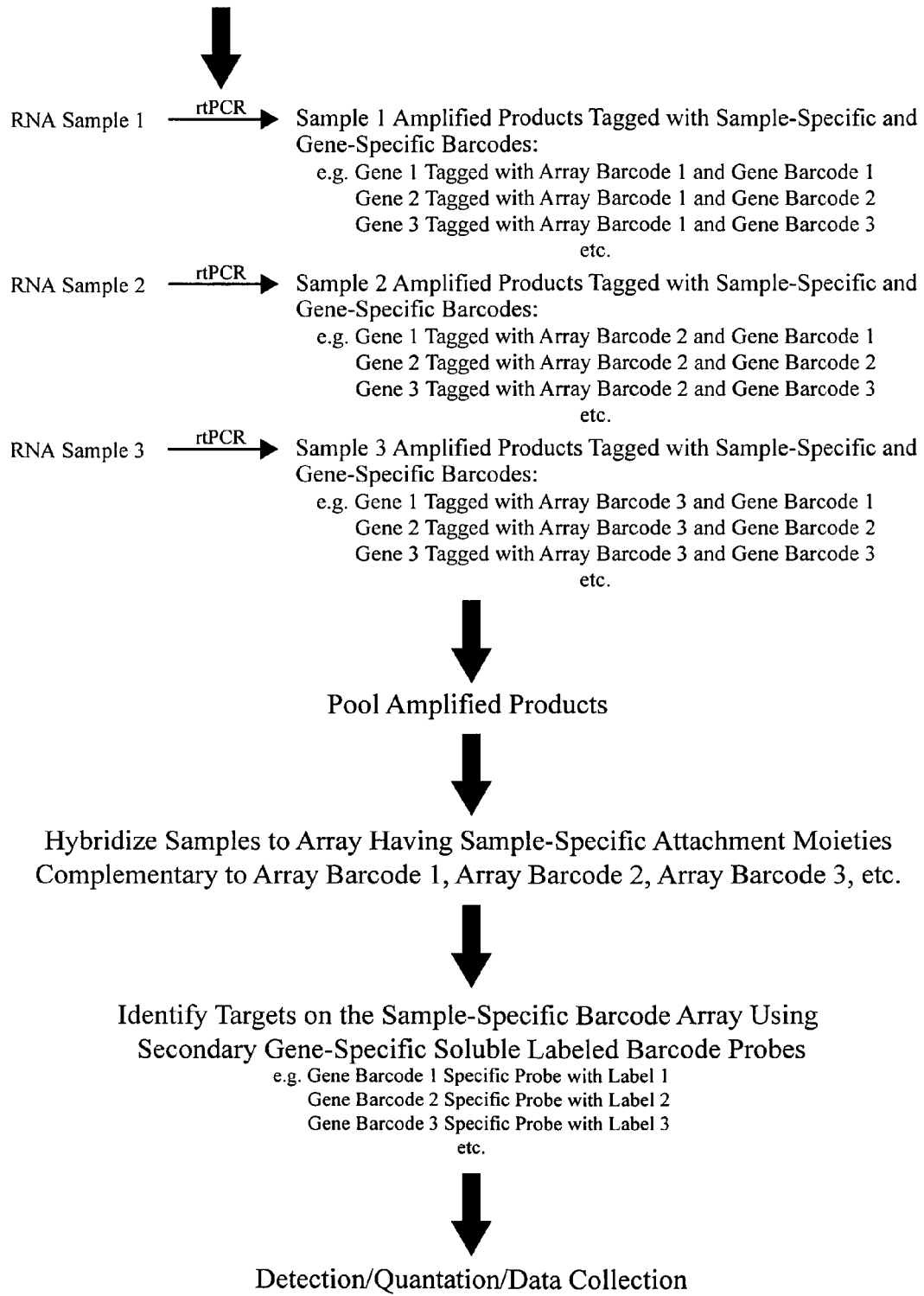

FIG. 8 illustrates a microarray-based expression profiling scheme using simultaneous sample-specific and gene-specific barcodes. RNA from various samples is reverse transcribed and amplified. The amplification is designed to use primers that will simultaneously incorporate a barcode into all the amplified products from each sample (i.e., in a sample-specific manner; the barcode for sample 1 is different from the barcode for sample 2, which is again different from the barcode for sample 3, etc.) as well as incorporate a gene-specific barcode for each targeted gene across samples (i.e., all amplicons for gene-1 receive gene barcode-1, including amplicons from samples 1, 2 and 3; all amplicons for gene-2 receive gene barcode-2, including amplicons from samples 1, 2 and 3; etc.). This labeling and detection strategy is similar to the situation shown in FIG. 5A.

Following amplification, the amplified products can be pooled and applied to a suitable array. In one embodiment (pictured in FIG. 8), the array comprises stationary probes (i.e., attachment moieties) specific for (i.e., complementary to) the various sample barcodes (array barcode-1, array barcode-2, array barcode-3, etc.). Such an array configuration can be considered a generic array. The resulting hybridization complexes can then be visualized using labeled, soluble (i.e., not affixed) gene-specific barcode probes (such probes can be considered generic labeled probes). Alternatively, the array can use gene-specific capture probes, and the resulting hybridization complexes can be detected using labeled soluble probes complementary to the sample-specific barcodes.

Figure 9:
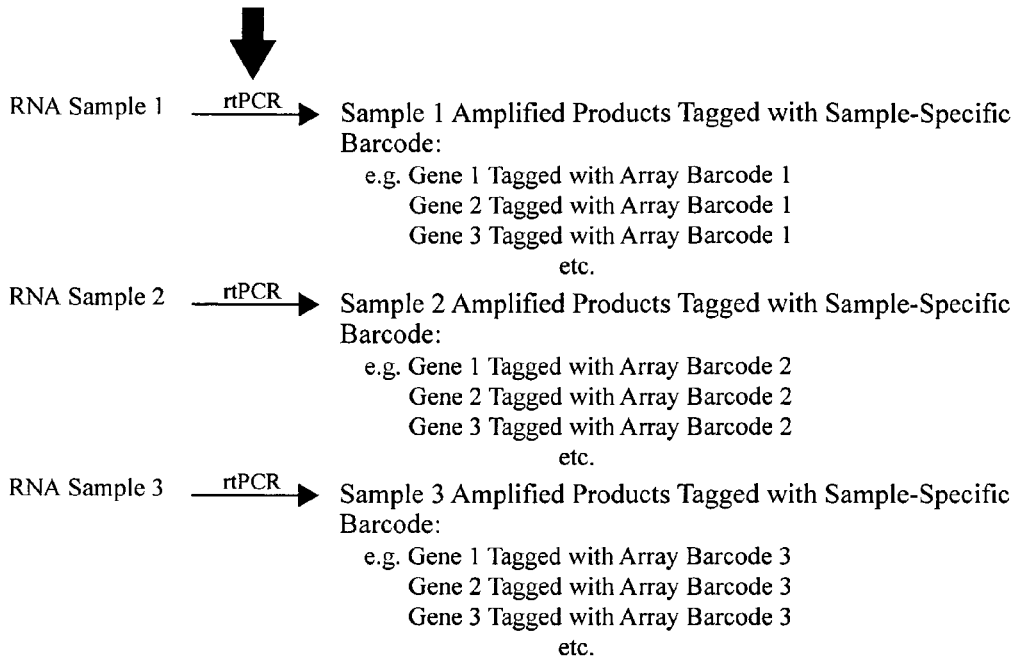

FIG. 9 illustrates a microarray-based expression profiling scheme using sample-specific barcodes in combination with gene-specific linker oligonucleotides (oligos). RNA from various samples is selectively reverse transcribed and amplified using gene specific primers, simultaneously incorporating a barcode in a sample-specific manner, i.e., the barcode for all amplicons from sample 1 is different from the barcode for all the amplicons from sample 2, which is again different from the barcode for all the amplicons from sample 3, etc.).

Figure 5A:
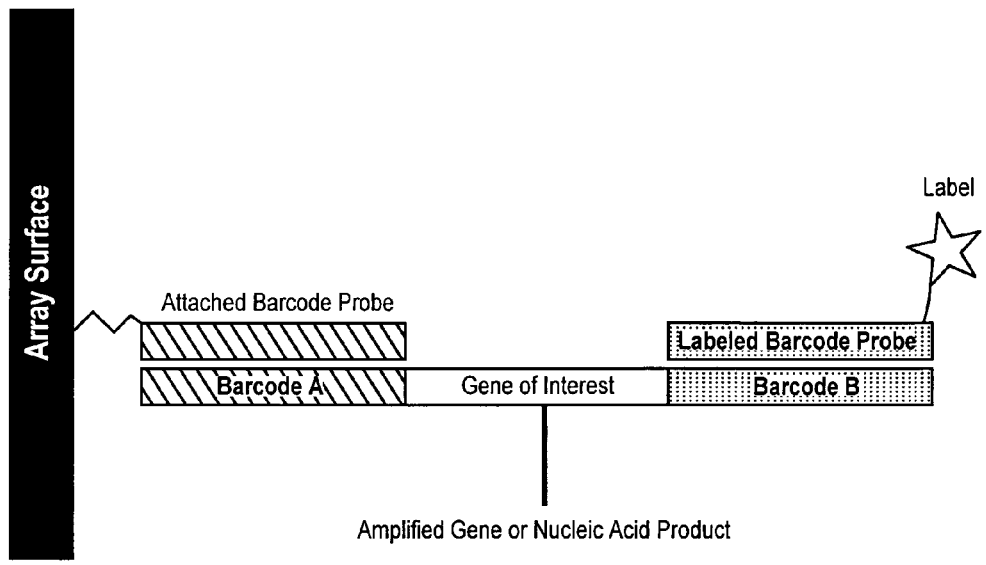
FIGS. 5A and 5B provide schematic representations of various aspects of the invention incorporating labeled soluble secondary probes and/or soluble linking oligomers in a barcode microarray.
Figure 5B:
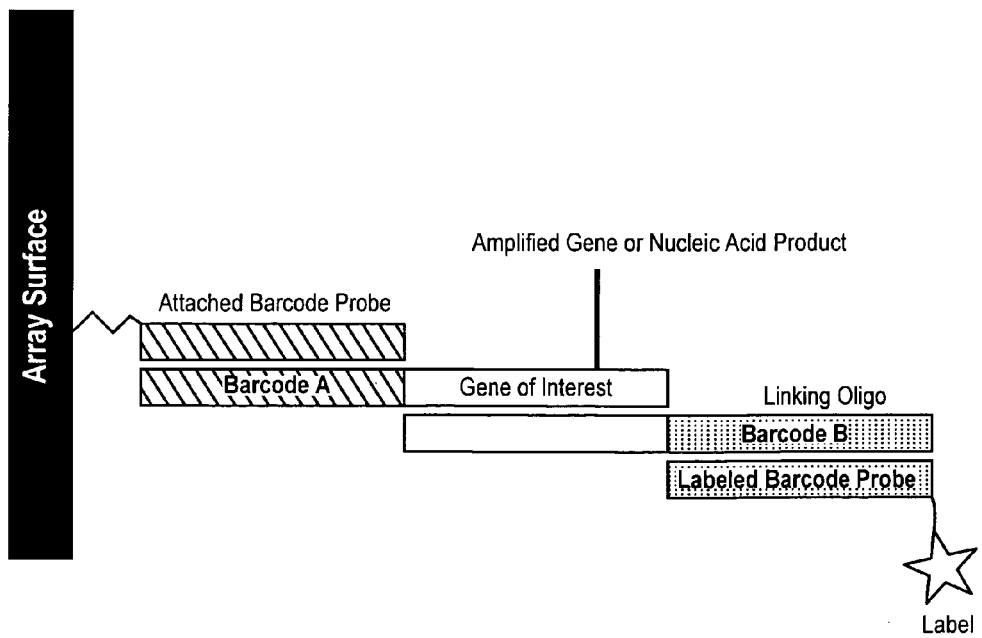

Following selective amplification, the amplified products are applied to a suitable array. In one embodiment (pictured in FIG. 9), the array comprises stationary probes (i.e., attachment moieties) specific for (i.e., complementary to) the various sample-specific barcode sequences. The resulting hybridization complexes are then hybridized with a suitable linker oligo that contains sequence complementary to the gene of interest and also sequence complementary to a suitable labeled soluble barcode probe. Following hybridization of the linker oligo, the tethered hybridization complexes having the linker oligos are visualized using a labeled soluble barcode probe complementary to the barcode on the linker oligo. This situation is depicted in FIG. 5B.

Figure 10:
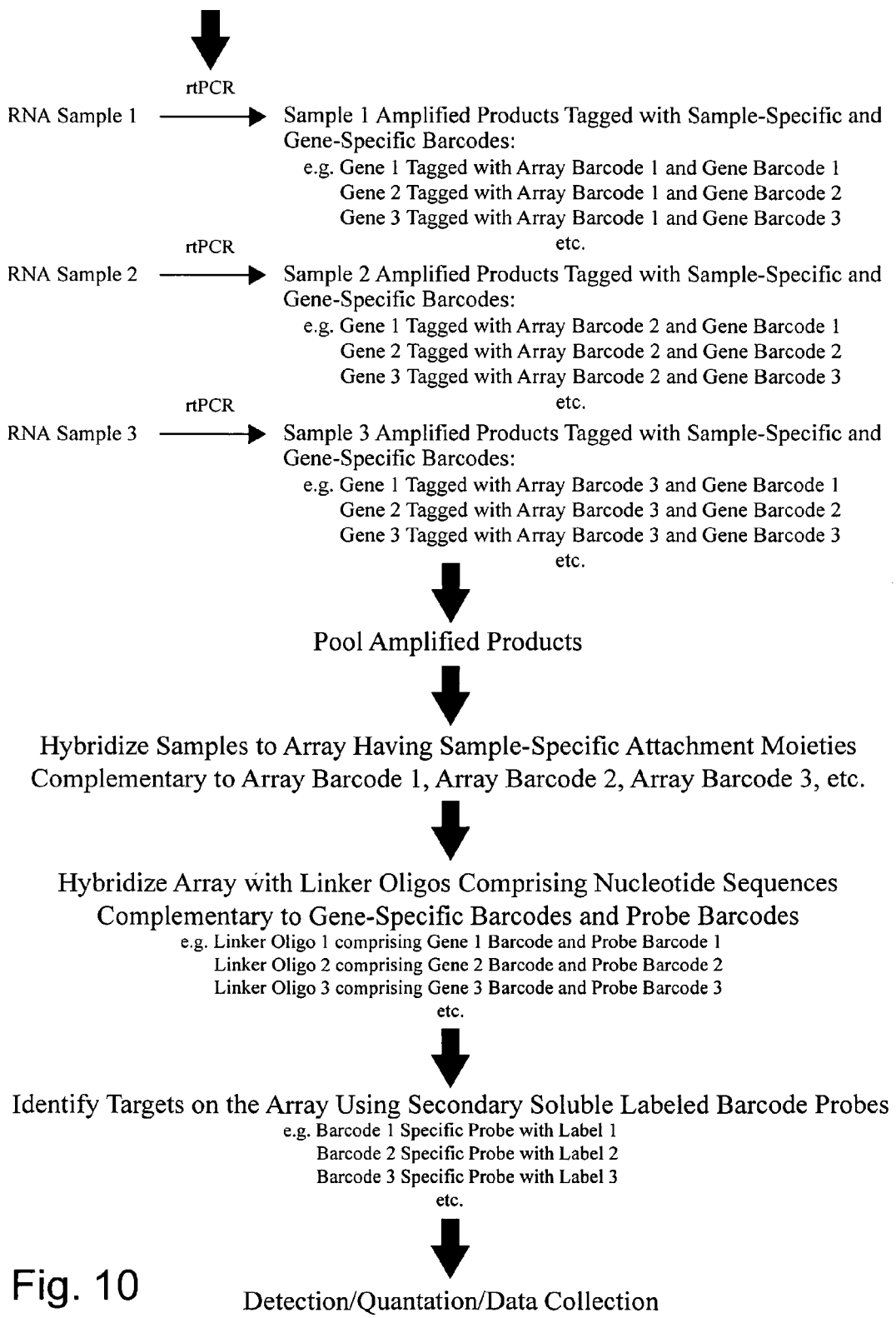

FIG. 10 illustrates a microarray-based expression profiling scheme similar to the linker oligo protocol described in FIG. 9, except using double-barcode strategy. RNA from various samples is selectively reverse transcribed and amplified using gene specific primers, simultaneously incorporating two barcodes into the amplicon; one barcode is incorporated in a sample-specific manner, i.e., the barcode for all amplicons from sample 1 is different from the barcode for all the amplicons from sample 2, which is again different from the barcode for all the amplicons from sample 3, etc.) and also incorporates a barcode in a gene-specific manner (i.e., the gene-1 amplicon contains barcode-1, the gene-2 amplicon contains barcode-2, the gene-3 amplicon contains barcode-3, etc.).

Following selective amplification, amplified products can be pooled and are then applied to a suitable array. In one embodiment (pictured in FIG. 10), the array comprises stationary probes (i.e., attachment moieties) specific for (i.e., complementary to) the various sample-specific barcode sequences. The resulting hybridization complexes are then hybridized with a suitable linker oligo containing two barcodes; namely, barcode sequence complementary to the gene-specific barcode and also sequence complementary to a suitable labeled soluble barcode probe. Following hybridization of the linker oligo, the tethered hybridization complexes having the linker oligos are visualized using a labeled soluble barcode probe complementary to the second barcode on the linker oligo.

Generic Arrays

In some embodiments, each of the different gene transcripts to be amplified can incorporate a barcode sequence that is specific and unique to each gene. These sequences can then be used as the point of hybridization with the microarray (i.e., the attachment moiety), wherein the microarray contains a plurality of oligonucleotide probes that are complementary to each of the different barcode sequences. The advantage of this process is that one can utilize a generic set of barcode sequences, both in the primer set and on the microarray, offering an opportunity to create a generic microarray that can be used over and over again to monitor the expression profiles (synonymous with expression patterns) of different genes.

Generic arrays consist of a plurality of oligonucleotide sequences that are spatially arrayed in two or more locations on a physical array. For each generic array the plurality of oligonucleotide sequences are repeated with each generic array being an identical or near identical copy. Multiple copies of a generic array represent a plurality of generic arrays, or arrays of arrays. An example of an array or arrays of generic arrays is the Beckman SNPstreaM™ 96-well plate wherein the generic arrays are each enclosed within a well of a microtiter plate, and each well consists of a plurality of oligonucleotides sequences, e.g. 52 different sequences. These same 52 sequences are arrayed in the same spatial order in each of the 96 wells of the microtiter plate. Other formats can be envisioned by one skilled in the art. For example, a generic array can be employed in the context of methods involving "flipping" the microarray paradigm as described in U.S. patent application Ser. No. 10/622,010 by Monforte, filed Jul. 16, 2003.

In this embodiment, a barcode sequence is introduced into each of at least a subset of sequences in a sample of nucleic acids corresponding to an expressed RNA sample derived from a biological sample. While it is generally convenient to incorporate such a barcode during an amplification process, one of skill in the art will appreciate that a barcode can be incorporated in a nucleic acid using alternative methods, such as a reverse transcriptase mediated process using a primer including the barcode sequence upstream of the transcriptase recognition sequence. For each of a given subset of unique RNA species in the sample, a different barcode sequence is introduced. The nucleic acids corresponding to the expressed RNAs of the biological sample are then hybridized to the generic array. Individual elements of the generic array can be probed to detect unique gene sequences using defined sequence probes corresponding to the target gene sequences, or, alternatively, with labeled barcode specific probes corresponding to a second barcode incorporated into the amplified nucleic acid, as shown in FIG. 5A.

Generic Probes

Labeled barcode probes are oligonucleotide sequences that possess a label. For a given set of experiments, a plurality of barcode probes, each with a unique oligonucleotide sequence can be prepared, wherein each unique sequence is associated with a different label. (e.g., by labeling different probes with fluorescent labels that can be uniquely identified by their absorption/emission properties). Alternatively, as shown in FIG. 5B, a linking oligonucleotide having a first subsequence (or segment) complementary to a gene specific sequence and a second subsequence comprising a barcode can be detected using a labeled barcode probe.

Sorting Samples by Hybridization

One embodiment of the screening method incorporates the use of a generic array to direct the different amplified products to different spatially arrayed locations within the physical array. For example, each of the different RNA or nucleic acid samples to be analyzed are amplified in such a way that all products within a particular sample are labeled with a bar code, i.e. sample 1 amplified products comprise barcode 1, sample 2 amplified products comprise barcode 2, sample 3 amplified products comprise barcode 3, and so on. The samples, 1, 2, 3, etc., which are amplified in separate reactions may be pooled and then co-hybridized to the generic array, wherein spatial position 1 in the generic array has an oligonucleotide complementary to barcode 1, spatial position 2 in the generic array has an oligonucleotide complementary to barcode 2, spatial position 3 in the generic array has an oligonucleotide complementary to barcode 3, and so on. The method provides a significant advantage over direct spotting of samples 1, 2, 3, etc. in that there is no need to purify or isolate the samples prior to hybridization simplifying the overall process.

Reducing Labeling Complexity

A significant cost in the use of microarray-type assays for gene expression and nucleic acid detection is associated with the synthesis of oligonucleotides comprising one or more labels. In order to reduce cost, some embodiments utilize a set of generic probes, wherein the probes comprise a barcode sequence (see FIGS. 5A and 5B). These barcode probe sequences are made complementary to barcode sequences that are either (i) incorporated into the amplified gene or nucleic acid product during amplification, or (ii) utilize an intermediary or linking oligonucleotide to connect, via hybridization, the barcode-incorporating, dye-labeled generic probe.

In one embodiment of scenario (i), illustrated in FIG. 5A, an amplified gene or nucleic acid product is produced comprising gene-specific sequence and two unique barcodes, barcode A and barcode B. Barcode A serves as a target for attachment to the array surface via a suitable complementary attached barcode probe. Barcode B on the amplified product serves as a target for detection, where that barcode B sequence is hybridized with a suitable labeled and complementary barcode B probe. Alternatively, instead of using a labeled probe specific for the barcode B sequence, a labeled probe can be synthesized that is complementary to the amplified gene sequence.

In one embodiment of scenario (ii), illustrated in FIG. 5B, an amplified gene or nucleic acid product is produced comprising gene-specific sequence and a unique barcode A. Barcode A on the amplified product serves as a target for attachment to the array surface via a suitable attachment probe complementary to barcode A. The target is then hybridized to a linking oligonucleotide comprising gene-specific sequence and a second unique barcode (barcode B in FIG. 5B). Barcode B is then detected and visualized by a labeled generic probe complementary to Barcode B. When an intermediary (or bridging or linking) oligonucleotide is used, the barcode probe comprises sequences complementary to both the amplified RNA/nucleic acid and the generic probe.

The generic arrays and generic probes can be used in combination or separately and offer advantages of simplifying the process (assay development and assay performance) and reducing assay costs.

Biological Samples

Expressed RNA samples for use in the methods of the present invention are obtained from a number of biological sources. Biological samples can either prokaryotic or eukaryotic in origin. For example, expressed RNA samples can be obtained from such biological sources as animals, plants, yeast, fungi, bacteria and viruses, and/or cells infected with viruses. Optionally, the expressed RNA samples can be collected from cells that have been treated with one or more members of a compound library. Biological samples in the context of the present invention include vertebrates, such as mammals, e.g., mice, rats, hamsters, guinea pigs, rabbits, cats, dogs, primates, humans, and non-mammalian vertebrates, such as amphibians, e.g., frogs, toads, and fish, such as zebra fish, and other species of scientific interest, as well as non-vertebrate species such as nematodes and insects, e.g., *Drosophila*. It is not intended that the invention be limited to RNA samples from any particular organism or cell type.

Most frequently, the biological source or sample is a cell line grown in culture, i.e., an immortalized strain of a cell obtained from a multicellular organism. Cell lines useful in the methods of the invention includes cell lines derived from, for example, one or more different types of tissues or tumors, primary cell lines, cells which have been subjected to transient and/or stable genetic modification, and the like. Optionally, the cells are mammalian cells, for example murine, rodent, guinea pig, rabbit, canine, feline, primate or human cells. Alternatively, the cells can be of non-mammalian origin, derived, for example, from frogs, amphibians, or various fishes such as the zebra fish.

Cell lines which can be used in the methods of the present invention include, but are not limited to, those available from cell repositories such as the American Type Culture Collection (on the world wide web at atcc.org), the World Data Center on Microorganisms (on the world wide web at wdcm.nig.ac.jp), European Collection of Animal Cell Culture (on the world wide web at ecacc.org) and the Japanese Cancer Research Resources Bank (on the world wide web at cellbank.nihs.go.jp). These cell lines include, but are not limited to, the following cell lines: 293, 293Tet-Off, CHO-AA8 Tet-Off, MCF7, MCF7 Tet-Off, LNCap, T-5, BSC-1, BHK-21, Phinx-A, 3T3, HeLa, PC3, DU145,ZR 75-1, HS 578-T, DBT, Bos, CV1, L-2, RK13, HTTA, HepG2, BHK-Jurkat, Daudi, RAMOS, KG-1, K562, U937, HSB-2, HL-60, MDAHB231, C2C12, HTB-26, HTB-129, HPIC5, A-431, CRL-1573, 3T3L1, Cama-1, J774A.1, HeLa 229, PT-67, Cos7, OST7, HeLa-S, THP-1, and NXA. Additional cell lines can be obtained, for example, from cell line providers such as Clonetics Corporation (Walkersville, Md.; on the world wide web at clonetics.com). Optionally, the expressed RNA samples are derived from cultured cells optimized for the analysis of a particular disease area of interest, e.g., cancer, inflammation, cardiovascular disease, infectious diseases, proliferative diseases, an immune system disorder (e.g., multiple sclerosis, diabetes, allergy), or a central nervous system disorder (e.g., Alzheimer's disease, Parkinson disease).

A variety of cell culture media for maintaining cells of interest in culture are described in *The Handbook of Microbiological Media*, Atlas and Parks (eds) (1993, CRC Press, Boca Raton, Fla.). References describing the techniques involved in bacterial and animal cell culture include Sambrook et al., *Molecular Cloning—A Laboratory Manual* (2nd Ed.), Vol. 1-3 (1989, Cold Spring Harbor Laboratory, Cold Spring Harbor, N.Y.); *Current Protocols in Molecular Biology*, F. M. Ausubel et al., eds., Current Protocols, (John Wiley & Sons, Inc., supplemented through 2002); Freshney, *Culture of Animal Cells, a Manual of Basic Technique*, third edition (1994, Wiley-Liss, New York) and the references cited therein; Humason, *Animal Tissue Techniques*, fourth edition (1979, W.H. Freeman and Company, New York); and Ricciardelli, et al. (1989) *In Vitro Cell Dev. Biol.* 25:1016-1024. Information regarding plant cell culture can be found in *Plant Cell and Tissue Culture in Liquid Systems*, by Payne et al. (1992, John Wiley & Sons, Inc. New York, N.Y.);*Plant Cell, Tissue and Organ Culture: Fundamental Methods* by Gamborg and Phillips, eds. (1995, Springer Lab Manual, Springer-Verlag, Berlin ), and is also available in commercial literature such as the *Life Science Research Cell Culture Catalogue* (1998) from Sigma-Aldrich, Inc. (St. Louis, Mo.) (Sigma-LSRCCC) and the *Plant Culture Catalogue* and supplement (1997) also from Sigma-Aldrich, Inc. (St. Louis, Mo.) (Sigma-PCCS).

For example, either primary or immortalized (or other) cell lines are grown in a master flask, then trypsinized (if they are adherent) and transferred to a 96-well plate, seeding each well at a density of $10^4$ to $10^6$ cells/well. If the gene expression profile in response to a chemical treatment is sought, the chemical agent of choice is prepared in a range of concentrations (further details regarding treatment with, e.g., compound or chemical libraries, is provided below). After a time of recovery and growth as appropriate for the cell line, cells are exposed to the chemical(s) or compound(s) for a period of time. Preferably, the period of exposure to the chemical(s) or compound(s) will not adversely impact the viability of the cells. Preferably, assays include a range of chemical concentrations and exposure times, and include replicate samples. After treatment, typically, the medium is removed and expressed RNA samples are prepared from the cells.

Although the example described above uses a master flask and a 96-well plate for the culture of cells, it is not intended that the invention be limited to these or any other format, configuration or vessel for the culture of cells. One of skill in the art will recognize that a large variety of cell culture apparatus is known in the art and is available for cell culture. Indeed, the choice of suitable culture conditions will be cell-type dependent, and will also depend on the nature of the experiment at hand. Other multi-well plate formats can be employed, for example but not limited to, 6, 12, 48, 384 and 1536 well plates. Culture formats that do not use conventional flasks (e.g., roller bottles, plates, bioreactors, etc.), as well as microtiter formats, are also contemplated.

The choice of cell lines employed in the methods of the present invention will vary based upon a number of factors, such as the objective of the study, the desired biological activity being modified, the disease area of interest, and the number of relevant cell lines available. Additional considerations, e.g., for screening compound libraries for potential drug targets, include, but are not limited to, the representation of diverse cell types (for example, the use of diverse cancer cell types for screening of cancer inhibitory compounds), previous usage in the study of similar compounds, and sensitivity or resistance to drug treatment. Optionally, the methods are performed in a high throughput, multiwell format.

In some circumstances, cell lines with one or more modifications in a biochemical or genetic pathway are employed. The difference between a modified (daughter) cell line and a parental (e.g. wild type) cell line can arise, for example, from changes in the "functional activity" of at least one biological molecule, for example, a protein or a nucleic acid. A difference in the functional activity of a biological molecule refers to an alteration in an activity and/or a concentration of that molecule, and can include, but is not limited to, changes in transcriptional activity, translational activity, catalytic activity, binding or hybridization activity, stability, abundance, transportation, compartmentalization, secretion, or a combination thereof. The functional activity of a biological molecule can also be affected by changes in one or more chemical modifications of that molecule, including but not limited to adenylation, glycosylation, phosphorylation, acetylation, methylation, ubiquitination, and the like.

The alteration in activity or concentration of the at least one biological molecule can also result from treatment of the parental cell line. Furthermore, the alteration in activity can be a temporary response to treatment, or can result in permanent change to cell physiology (e.g., a mutation or an irreversible structural modification). The particular activity that is altered or particular cell growth characteristics that are affected are in no way limited. For example, cell treatment or modification can result in cell growth stimulation, cell growth inhibition, or stimulation or inhibition of any particular enzymatic activity or biochemical pathway. Temporary alterations can be produced by treatment with a variety of chemical stimulatory and inhibitory molecules, as well as by proteins such as cell surface receptor ligands, antibodies, oligonucleotides, ribozymes, and/or vectors employing inducible, gene-specific knock in and knock down technologies. Alternatively, cells can be treated with DNA damaging agents such as, intercalating agents such as ethidium bromide; alkylating agents such as ethylnitrosourea and methyl methanesulfonate; hydrogen peroxide; UV irradiation, and gamma irradiation. Examples of oxidative stress agents include, but are not limited to, hydrogen peroxide, superoxide radicals, hydroxyl free radicals, perhydroxyl radicals, peroxyl radicals, alkoxyl radicals, and the like. Examples of metabolic blocking and/or energy blocking agents include, but are not limited to, azidothymidine (AZT), ion (e.g. $Ca^{++}$, $K^+$, $Na^+$) channel blockers, $\alpha$ and $\beta$ adrenoreceptor blockers, histamine blockers, and the like. Examples of chemical inhibitors include, but are not limited to, receptor antagonists and inhibitory metabolites/catabolites (for example, mavelonate, which is a product of and in turn inhibits HMG-CoA reductase activity).

In some cases, it is optionally desirable to subject the cell line (or other biological sample) to one or more environmental stimuli that affect gene expression prior to treating with a compound library. For example, a cell line can optionally be exposed to an environmental condition (or change in an environmental condition) that results in activation or suppression or one or more genetic or biochemical pathways. Exemplary environmental stimuli include changes in growth media and nutritional status, temperature, changes in pH, changes in oxygen tension, changes in carbon dioxide tension, changes in gas composition, changes in atmospheric pressure or exposure to light, e.g., visible, ultraviolet, or infrared radiation. Alternatively, environmental stimuli include agents which either directly or indirectly influence gene expression, including, e.g., solvents.

In some cases, expression of one or more genes in the biological sample (e.g., cells, tissue or organism) is artificially altered prior to treating the sample with members of a compound library. Typically, such an alteration is induced to enhance the utility of the biological sample as a model system in which to test for physiological effects induced by members of a compound library.

For example, procedures which alter the genome of the biological sample in a permanent manner, such as insertional mutagenesis, deletion of genomic DNA, targeted gene disruption, introduction of a genomic or episomal vector, and the like can be used to alter expression of one or more genes in a biological sample in a manner which increases its utility as a model, e.g., for compound library screening. Similarly, processes that alter expression by interacting with DNA or RNA, such as transcription blocking, antisense DNA or RNA, iRNA, ribozymes, DNA binding oligonucleotides and zinc finger proteins, can be used to impact the expression of one or more genes in the biological sample prior to treating the sample with a member of a compound library.

Permanent genetic alteration can be produced by a variety of well known mutagenesis procedures, e.g., to generate mutant or variant cell lines. A variety of mutagenesis protocols, such as viral-based mutational techniques, homologous recombination techniques, gene trap strategies, inaccurate replication strategies, and chemical mutagenesis, are available and described in the art. These procedures can be used separately and/or in combination to produce modified cell lines for use in the methods of the present invention. See, for example, Amsterdam et al. "A large-scale insertional mutagenesis screen in zebrafish" Genes Dev 1999 October 13:2713-2724; Carter (1986) "Site-directed mutagenesis" Biochem. J. 237:1-7; Crameri and Stemmer (1995) "Combinatorial multiple cassette mutagenesis creates all the permutations of mutant and wildtype cassettes" BioTechniques 18:194-195; Inamdar "Functional genomics the old-fashioned way: chemical mutagenesis in mice"Bioessays 2001 February 23:116-120; Ling et al. (1997) "Approaches to DNA mutagenesis: an overview" Anal Biochem. 254(2): 157-178; Napolitano et al. "All three SOS-inducible DNA polymerases (Pol II, Pol IV and Pol V) are involved in induced mutagenesis" EMBO J 2000 November 19:6259-6265; and Rathkolb et al. "Large-scale N-ethyl-N-nitrosourea mutagenesis of mice--from phenotypes to genes" Exp Physiol 2000 November 85:635-44. Furthermore, kits for mutagenesis and related techniques are also available from a number of commercial sources (see, for example, Stratagene (La Jolla, Calif.; on the world wide web at stratagene.com/vectors/index2.htm), BD Biosciences Clontech (Palo Alto, Calif.; on the world wide web at clontech.com/retroviral/index.shtml), and the Gateway® cloning system from Invitrogen™ (Carlsbad, Calif.; on the world wide web at invitrogen.com) General texts which describe molecular biological techniques useful in the generation of modified cell lines, including mutagenesis, include Berger and Kimmel; Sambrook et al., and Ausubel et al., all supra. Further details regarding the generation of modified cell lines can be found in, e.g., published PCT international applications WO 02/08466 by Monforte, entitled "A SYSTEMATIC APPROACH TO MECHANISM-OF-RESPONSE ANALYSES," and WO 01/71023 by Monforte et al., entitled "A SYSTEMATIC APPROACH TO THE ANALYSIS OF GENE FUNCTION."

Alternatively, procedures for making targeted gene mutations can be employed to modify cell lines prior to treating with members of a compound library. For example, a gene can be prevented from expressing any protein (knockout) via a number of processes, including deletion of the gene or transcription promoting elements for the gene at the DNA level within the cell. Knockout modifications generally involve modification of the gene or genes within the genome (see, for example, Gonzalez (2001) "The use of gene knockout mice to unravel the mechanisms of toxicity and chemical carcinogenesis"Toxicol Lett., 120:199-208). Knockouts can be either heterozygous (e.g. inactivating only one copy of the gene) or homozygous (inactivating both copies of the gene). One exemplary database of mouse knockouts can be found on the world wide web at research.bmn.com (the BioMedNet mouse knockout and mutation database). A knockout phenotype can also be mimicked by antisense gene expression and RNAi technologies, all of which find use with the invention.

Optionally, following (or in conjunction with) mutagenesis procedures, cell lines with desired modifications are typically selected using one or more experimental techniques to identify and isolate cells which have been altered in the desired manner. For example, the selection process can include, but is not limited to: identifying cells that survive and/or continue to grow under different environments, stresses and/or stimulation; cells that have increased or decreased expression of a particular protein that can be used to sort or separate cells with the altered protein levels, (e.g. using flow cytometry to sort cells that are over expressing a particular cell surface receptor); and cells that have an altered phenotype that can be identified and selected, e.g. cells arrested in a particular cycle phase, cells that have altered ability to invade a barrier or translocate, cells that have a different shape, or have or have not differentiated into a different cell type). Numerous additional selection methods are known to one of skill in the art and can be employed to provide cell lines for use in the methods of the present invention.

Isolation of Expressed RNA Samples

Expressed RNA samples are isolated from biological samples using any of a number of well-known procedures. For example, biological samples can be lysed in a guanidinium-based lysis buffer, optionally containing additional components to stabilize the RNA. In some embodiments of the present invention, the lysis buffer also contains purified RNAs as controls to monitor recovery and stability of RNA from cell cultures. Examples of purified RNA templates for use as control RNA species include the Kanamycin Positive Control RNA from Promega Corporation (Madison, Wis.), and 7.5 kb Poly(A)-Tailed RNA from Gibco/Life Technologies (Rockville, Md.). Lysates can be used immediately or stored frozen at, e.g., −80° C.

Optionally, total RNA is purified from cell lysates (or other types of samples) using silica-based isolation in an automation-compatible, 96-well format, such as the RNeasy® purification platform (Qiagen, Inc.; Valencia, Calif.). Alternatively, RNA is isolated using solid-phase oligo-dT capture using oligo-dT bound to microbeads or cellulose columns. This method has the added advantage of isolating mRNA from genomic DNA and total RNA, and allowing transfer of the mRNA-capture medium directly into the reverse transcriptase reaction. Additional RNA isolation methods are also contemplated, for example but not limited to, extraction with silica-coated beads. Further methods for RNA isolation and preparation are well known or can be devised by one skilled in the art.

Alternatively, the methods of the present invention are performed using crude cell lysates, eliminating the need to isolate RNA. RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at very low levels, the background can be eliminated by treating the samples with a suitable DNase, or by using primers that target splice junctions for subsequent priming of cDNA or amplification products. For example, one of the two target-specific primers could be designed to span a splice junction, thus excluding DNA as a template. As another example, the two target-specific primers are designed to flank a splice junction, generating larger PCR products for DNA or unspliced mRNA templates as compared to processed mRNA templates. One skilled in the art could design a variety of specialized priming applications that would facilitate use of crude extracts as samples for the purposes of this invention.

It is not intended that the present invention be limited to any particular method for RNA isolation, reagents for RNA isolation, source of RNA for reverse transcription and amplification (rtPCR), or sources of RNA for standardization or positive controls. One of skill in the art will recognize that a variety of alternative protocols and regents known in the art all find use with the invention, and furthermore, can be used without departing from the scope of the invention.

Nucleic Acids Corresponding to Expressed RNA Samples

In some embodiments of the present invention, nucleic acids derived from RNA samples are applied to arrays, or arrays of arrays, that comprise logically or spatially arrayed nucleic acid probes (e.g., nucleic acid probes immobilized on a solid support). Although expressed RNA samples can be applied to an array (or to arrays of arrays) directly, e.g., on the surface of a glass microarray slide, it is generally desirable to employ DNA products corresponding to the expressed RNA sample to improve stability and ease of handling. In some instances, cDNA products generated by the reverse transcription of the expressed RNA in the samples is done according to well established procedures, e.g., as described in Sambrook, Ausubel, etc. are arrayed. More typically, DNA products corresponding to expressed RNA samples are amplified prior to exposure to an array to improve the sensitivity and dynamic range of the assay.

Expressed RNA samples can be reverse transcribed using non-specific primers, such as an anchored oligo-dT primer, or random sequence primers. An advantage of this approach is that the mRNA sample maintains an "unfractionated" quality because the sites of priming are non-specific, i.e., the products of this RT reaction will serve as template for any desired target in the subsequent PCR amplification. An additional advantage of this approach is that samples to be archived are stored in the form of DNA, which is more resistant to degradation than RNA. In certain methods (e.g., described in U.S. Pat. No. 5,962,271 to Chenchik et al., entitled "METHODS AND COMPOSITIONS FOR GENERATING FULL-LENGTH cDNA HAVING ARBITRARY NUCLEOTIDE SEQUENCE AT THE 3'-END," and commercially available kits supplied by, for example, Clontech (Palo Alto, Calif.), reverse transcription of a full length mRNA is initiated using an oligo-dT primer. A cap switching oligonucleotide primer is annealed to the 5' cap of the mRNA which serves as a template for the nascent strand as it approaches the end of mRNA template. The cap switching oligonucleotide primer includes in addition to the sequence that permits it to bind to the cap, a polynucleotide sequence that serves as a primer annealing site in subsequent amplification reactions.

Alternatively, RNA is converted to cDNA using a target-specific primer complementary to the RNA for each gene target for which expression data is desired. Methods for reverse transcription also include, the use of thermostable DNA polymerases, as described in the art. As an exemplary embodiment, avian myeloblastosis virus reverse transcriptase (AMV-RT), or Maloney murine leukemia virus reverse transcriptase (MoMLV-RT) is used, although other enzymes are contemplated. An advantage of using target-specific primers in the RT reaction is that only the desired (e.g., targeted) sequences are amplified, and consequently, exposed to the array, or optionally, used in subsequent amplification reactions.

Amplification of DNA products corresponding to expressed RNA samples can be accomplished using the polymerase chain reaction (PCR), which is described in detail in U.S. Pat. No. 4,683,195 (Mullis et al.), U.S. Pat. No. 4,683,202 (Mullis), and U.S. Pat. No. 4,800,159 (Mullis et al.), and in *PCR Protocols A Guide to Methods and Applications* (Innis et al., eds.) Academic Press Inc. San Diego, Calif. (1990), see also, Sambrook, Ausubel. PCR utilizes pairs of primers having sequences complimentary to opposite strands of target nucleic acids, and positioned such that the primers are converging. The primers are incubated with template DNA under conditions that permit selective hybridization. Primers can be provided in double-stranded or single-stranded form, although the single-stranded form is preferred. If the target gene(s) sequence is present in a sample, the primers will hybridize to form a nucleic-acid: primer complex. An excess of deoxynucleoside triphosphates is added, along with a thermostable DNA polymerase, e.g. Taq polymerase. If the target gene(s):primer complex has been formed, the polymerase will extend the primer along the target gene(s) sequence by adding nucleotides. After polymerization, the newly-synthesized strand of DNA is dissociated from its complimentary template strand by raising the temperature of the reaction mixture. When the temperature is subsequently lowered, new primers will bind to each of these two strands of DNA, and the process is repeated. Multiple cycles of raising and lowering the temperature are conducted, with a round of replication in each cycle, until a sufficient amount of amplification product is produced.

In some embodiments, RNA in an RNA sample is reverse transcribed to yield cDNA and then is amplified in a single reaction that couples reverse transcription and PCR, a process generally termed "rtPCR." Protocols that utilize rtPCR use either gene specific primers to selectively amplify particular gene sequences, or use random or semi-random primers for the amplification of the global population of mRNAs or some subset based on the presence of particular sequences or sequence motifs (see, e.g., US Pat. No. 5,962,271 to Chenchik et al., entitled "METHODS AND COMPOSITIONS FOR GENERATING FULL-LENGTH cDNA HAVING ARBITRARY NUCLEOTIDE SEQUENCE AT THE 3'-END,"). The techniques described in U.S. Pat. No. 5,962,271 provide for the ability to multiplex to very high levels.

Alternative methods for amplifying nucleic acids corresponding to expressed RNA samples include, e.g., transcription-based amplification systems (TAS), such as that first described by Kwoh et al. (Proc. Natl. Acad. Sci. (1989) 86(4): 1173-7), or isothermal transcription-based systems such as 3SR (Self-Sustained Sequence Replication; Guatelli et al. (1990) Proc. Natl. Acad. Sci. 87:1874-1878) or NASBA (nucleic acid sequence based amplification; Kievits et al. (1991) J Virol Methods 35(3):273-86). In these methods, one or more mRNA targets of interest are copied into cDNA by a reverse transcriptase. The primer(s) for cDNA synthesis includes the promoter sequence of a designated DNA-dependent RNA polymerase 5' to the primer's region of homology with the template. In some procedures a second complementary cDNA strand is synthesized using, e.g., a hairpin loop structure formed by the initially synthesized cDNA strand (see, e.g., U.S. Pat. No. 5,545,522 to Van Gelder et al., entitled "PROCESS FOR AMPLIFYING A TARGET POLY-NUCLEOTIDE SEQUENCE USING A SINGLE PRIMER-PROMOTER COMPLEX. Alternatively, a second strand is synthesized from a primer complementary to a primer sequence added by template switching to an oligonucleotide that anneals to the 5' cap structure of a full-length mRNA (SMART™ Amplification described in Chenchik et al., U.S. Pat. No. 5,962,271). The resulting cDNA products can then serve as templates for multiple rounds of transcription by the appropriate RNA polymerase. Transcription of the cDNA template rapidly amplifies the signal from the original target mRNA. The isothermal reactions bypass the need for denaturing cDNA strands from their RNA templates by including RNAse H to degrade RNA hybridized to DNA. Other methods using isothermal amplification, including, e.g., methods described in U.S. Pat. No. 6,251,639, are also favorably employed in the context of the present invention.

Alternatively, amplification is accomplished by used of the ligase chain reaction (LCR), disclosed in European Patent Application No. 320,308 (Backman and Wang), or by the ligase detection reaction (LDR), disclosed in U.S. Pat. No. 4,883,750 (Whiteley et al.). In LCR, two probe pairs are prepared, which are complimentary to each other, and to adjacent sequences on both strands of the target. Each pair will bind to opposite strands of the target such that they are adjacent. Each of the two probe pairs can then be linked to form a single unit, using a thermostable ligase. By temperature cycling, as in PCR, bound ligated units dissociate from the target, then both molecules can serve as "target sequences" for ligation of excess probe pairs, providing for an exponential amplification. The LDR is very similar to LCR. In this variation, oligonucleotides complimentary to only one strand of the target are used, resulting in a linear amplification of ligation products, since only the original target DNA can serve as a hybridization template. It is used following a PCR amplification of the target in order to increase signal.

Additional suitable methods include, but are not limited to, strand displacement amplification (Walker et al. (1992) Nucleic Acids Res. 20:1691-1696), repair chain reaction (REF), cyclic probe reaction (REF), solid-phase amplification, including bridge amplification (Mehta and Singh (1999) BioTechniques 26(6): 1082-1086), rolling circle amplification (Kool, U.S. Pat. No. 5,714,320), rapid amplification of cDNA ends (Frohman (1988) Proc. Natl. Acad. Sci. 85: 8998-9002), the "invader assay" (Griffin et al. (1999) Proc. Natl. Acad. Sci. 96: 6301-6306), and methods for simultaneous amplification and detection as described in, e.g., U.S. Pat. Nos. 5,914,230 and 6,365,346.

Amplification of expressed RNA samples can be performed using random or semi-random primers to globally amplify a diverse population of expression products, or can be performed using target specific primers to amplify one or more selected expression products. Selective amplification of expression products using target specific primers can be performed in reactions that amplify a single product or that amplify a plurality of products, i.e., multiplex amplification reactions. When one or a small number of expression products is amplified in a single reaction, the products of multiple reactions can be combined or pooled for arraying, if desired. Similarly, a single expressed RNA sample (i.e., from a single biological sample) can be amplified in multiple target specific reactions which are then arrayed in more than one location of an array. Both of these variations increase the number of probes which can be analyzed in a single physical array.

Multiplex Amplification Strategies

An embodiment of the methods of the present invention involves the use of various PCR multiplexing strategies that are made possible by the combined use of target-specific (e.g., gene specific) and universal primers. These procedures are variations on the RT-PCR assays involving the reverse transcription of a single or double stranded DNA template corresponding to one or more expressed RNA species, followed by amplification in a PCR. Additional details regarding multiplex PCR strategies are found in, e.g., International PCT Patent Application WO 01/55454 by Loehrlein et al; and, U.S. Pat. No. 5,962,271 to Chenchik et al.

Multiplex amplification of a plurality of target sequences typically involves combining the plurality of target sequences with a plurality of target-specific primers (i.e., primers complementary to at least one strand of a reverse transcribed cDNA target sequence) and one or more universal primers, to produce a plurality of amplification products. A multiplex set of target sequences optionally comprises between about two targets and about 100 targets. In one embodiment of the present invention, the multiplex reaction includes at least 5 target sequences, but preferably at least ten targets or at least fifteen targets. Multiplexes of much larger numbers (e.g., about 20, about 50, about 75 and greater) are also contemplated.

In one embodiment of the methods of the present invention, at least one of the amplification targets in the multiplex set is a transcript that is endogenous to the sample and has been independently shown to exhibit a fairly constant and stable expression level (for example, a "housekeeping" gene, $\beta$-actin) during cell treatment or cell exposure to a compound or stimulus. The signal from this endogenous reference sequence provides a control for converting signals of other gene targets into relative expression levels. Optionally, a plurality of control mRNA targets/reference sequences that have relatively non-fluctuating expression levels may be included in the multiplexed amplification to serve as controls for each other. Alternatively, a defined quantity of an exogenous purified RNA species is added to the multiplex reaction or to the cells, for example, with the lysis reagents. Almost any purified, intact RNA species can be used, e.g. the Kanamycin Positive Control RNA or the 7.5 kb Poly(A)-Tailed RNA mentioned previously. This exogenously-added amplification target provides a way to monitor the recovery and stability of RNA from cell cultures. It can also serve as an exogenous reference signal for converting the signals obtained from the sample mRNAs into relative expression levels. In still another embodiment, a defined quantity of a purified DNA species is added to the PCR to provide an exogenous reference target for converting the signals obtained from sample mRNA targets into relative expression levels.

In one embodiment of the present invention, once the targets that comprise a multiplex set are determined, primer pairs complementary to each target sequence are designed, including both target-specific and universal primers. This can be accomplished using any of several software products that design primer sequences, such as OLIGO (Molecular Biology Insights, Inc., CO), Gene Runner (Hastings Software Inc., NY), or Primer3 (The Whitehead Institute, MA). Gene specific primers (GSPs) include at least two portions. The first portion includes a region complementary to a selected "universal sequence." The universal sequence is utilized to allow amplification of multiple targets (having divergent sequences) while using the same primer (e.g., the UP). The universal sequence is contained only in the primers, and preferably is not present in any nucleic acid (or complement thereof) provided by the sample being tested. A second portion of the GSPs, within the 3' region of the sequence, is complementary to and will hybridize with one of a plurality of designated target sequences. Although a single universal primer is described in the example provided above, multiple universal primers having different or unique sequences or labels can be employed in the methods of the present invention. If a single UP is used, the universal sequence will be the same within all GSPs. If a UP pair is to be used, the universal sequence will be different in the forward and reverse primers of the GSPs. The UP may also contain a detectable label on at least one of the primers, such as a fluorescent chromaphore.

Both the target-specific and universal sequences are of sufficient length and sequence complexity to form stable and specific duplexes, allowing amplification and detection of the target gene. In early rounds of the amplification, replication is primed primarily by the GSPs. The first round will add the universal sequence to the 5' regions of the amplification products. The second cycle will generate sequence complementary to the universal sequence within the 3' region of the complementary strand, creating a template that can be amplified by the universal primers alone. Optionally, the reaction is designed to contain limiting amounts of each of the GSPs and a molar excess of the UP, such that the UP will generally prime replication once its complementary sequence has been established in the template. The molar excess of UP over a GSP can range from about 5:1 to about 100:1; optionally, the reaction utilizes approximately 10:1 molar excess of UP over the amount of each GSP. Because all of the GSPs contain the same universal sequence, the same universal primer will amplify all targets in the multiplex, eliminating the quantitative variation that results from amplification from different primers.

The templates are initially single-stranded mRNA molecules, but eventually are predominantly DNA amplification products that serve as template in subsequent cycles. Messenger RNA is converted to cDNA by the action of reverse transcriptase polymerization from the target-specific reverse primers, or from a random or degenerate primer that results in global reverse transcription of the constituents of an expressed RNA sample. If a single stranded cDNA template has been synthesized, the target-specific forward primers and the universal forward and reverse primers are added along with a thermostable polymerase to generate the second strand of cDNA, followed by PCR amplification. The UP can anneal to target DNA only after its complementary universal sequence is added to the opposite strand through replication across the 5' region of the gene specific primer (GSP).

The length of complementary sequence between each primer and its binding partner (i.e. the target sequence or the universal sequence) should be sufficient to allow hybridization of the primer only to its target within a complex sample at the annealing temperature used for the PCR. A complementary sequence of, for example, about 15, 16, 17, 18, 19, 20, 21, 22, 23, 24, or 25 or more nucleotides is preferred for both the target-specific and universal regions of the primers. A particularly preferred length of each complementary region is about 20 bases, which will promote formation of stable and specific hybrids between the primer and target.

Optionally, primers are designed such that the annealing temperature of the universal sequence is higher/greater than that of the target-specific sequences. Methods employing these primers further include increasing the annealing temperature of the reaction after the first few rounds of amplification. This increase in reaction temperature suppresses further amplification of sample nucleic acids by the GSPs, and drives amplification by the UP. Depending on the application envisioned, one skilled in the art can employ varying conditions of hybridization to achieve varying degrees of selectivity of primer towards the target sequence. For example, varying the stringency of hybridization or the position of primer hybridization can reveal divergence within gene families.

Optionally, each candidate primer is shown or proven to be compatible with the other primers used in a multiplex reaction. In a preferred embodiment, each target-specific primer pair produces a single amplification product of a predicted size from a sample minimally containing all of the targets of the multiplex, and more preferably from a crude RNA mixture. Preferably, amplification of each individual target by its corresponding primers is not inhibited by inclusion of any other primers in the multiplex. None of the primers, either individually or in combination, should produce spurious products. These issues are easily addressed by one of skill in the art without the need for excessive experimentation.

Oligonucleotide primers are typically prepared by the phosphoramidite approach. In this automated, solid-phase procedure, each nucleotide is individually added to the 5'-end of the growing oligonucleotide chain, which is in turn attached at the 3'-end to a solid support. The added nucleotides are in the form of trivalent 3'-phosphoramidites that are protected from polymerization by a dimethoxytrityl ("DMT") group at the 5'-position. After base induced phosphoramidite coupling, mild oxidation to give a pentavalent phosphotriester intermediate and DMT removal provides a new site for oligonucleotide elongation. These syntheses may be performed on, for example, a Perkin Elmer/Applied Biosystems Division DNA synthesizer. The oligonucleotide primers are then cleaved off the solid support, and the phosphodiester and exocyclic amino groups are deprotected with ammonium hydroxide.

Elimination of Variations in Primer Annealing Efficiency

Variations in primer length and sequence can have a large impact on the efficiency with which primers anneal to their target and prime replication. In a typical multiplexed reaction in which each product is amplified by a unique primer pair, the relative quantities of amplified products may be significantly altered from the relative quantities of targets due to difference in annealing efficiencies. Embodiments of the methods of the present invention that couple the use of target-specific primers and universal primers eliminates this bias, producing amplification products that accurately reflect relative mRNA levels.

Attenuation of Strong Signals

The set of targets included in a multiplex reaction generally all yield signal strengths within the dynamic range of the detection platform used in order for quantitation of gene expression to be accurate. In some embodiments, it may be desirable or necessary to include a highly expressed gene (i.e., a gene that is more highly expressed than other genes) in a multiplex assay. However, the highly-expressed gene can interfere with quantitation for other genes expressed at very low levels if its signal of the highly expressed gene is not attenuated. One of skill in the art knows well that there are various ways to circumvent this technical problem, all of which find use with the invention. It is not intended that the invention be limited to any particular strategy for dealing with the technical issue of incorporating a highly transcribed gene in a multiplex amplification reaction.

In some embodiments, the most straight-forward solution to this technical problem is simply to limit the concentration of the amplification primers (e.g., the gene specific primers) for that abundant transcript in the rtPCR amplification step. Alternatively, other techniques are also known, and the invention teaches ways for attenuating the signals of relatively abundant target(s) during the amplification reaction such that they can be included in a multiplexed set without impacting the accuracy of quantitation of that set.

For example, amplification primers are optionally used that block polymerase extension of the 3' end of the primer. One preferred embodiment is modification of the 3'-hydroxyl of the oligonucleotide primer by addition of a phosphate group.

Another preferred embodiment is attachment of the terminal nucleotide via a 3'-3' linkage. One skilled in the art can conceive of other chemical structures or modifications that can be used for this purpose. The modified and the corresponding unmodified primer for the highly abundant target are mixed in a ratio empirically determined to reduce that target's signal, such that it falls within the dynamic range of other targets of the multiplex. Preferably, the reverse target-specific primer is modified, thereby attenuating signal by reduction of the amount of template created in the reverse transcriptase reaction.

Another embodiment for signal attenuation entails use of a target-specific primer that contains the target-specific sequence, but no universal primer sequence. This abbreviated primer (lacking the universal sequence) and the corresponding primer containing the universal sequence within the 5' region are mixed in a ratio empirically determined to reduce that target's signal, such that it then falls within the dynamic range of other targets of the multiplex system.

Purification of rtPCR Products

It is often desirable to "purify" the population of nucleic acids corresponding to expressed RNA samples (e.g., rtPCR products), prior to deposit on an array, due to presence of contaminants and salts. Numerous approaches to purifying nucleic acids, such as PCR products, exist with the two principle high throughput approaches being filtration in microtiter-plate format and magnetic bead capture and washing. For example, the Millipore Montage PCR96 DNA purification plates (and comparable 384-well version of this plate) are favorably employed in the context of the present invention. The protocol for use involves a simple one-step vacuum filtration and elution of the PCR products, and is compatible with automated systems, such as the Biomek Multimek system. Alternatively, magnetic bead capture and washing approaches can be adapted for an automated platform. It is not intended that the invention be limited to any particular technique(s) for purifying the nucleic acids of the invention (e.g., the amplified rtPCR products). One of skill knows well a variety of alternative techniques for purifying nucleic acids, all of which find use with the invention.

Array Format

Nucleic acids sets corresponding to expressed RNA samples, whether RNA, cDNA or amplification products (e.g., amplified rtPCR products), are generally applied (i.e., hybridized) to immobilized and spatially or logically arrayed assemblages of nucleic acid probes (generally termed arrays or microarrays), where the array comprises a nucleic acid probe or probes that are complementary to a member or members of the set of expressed RNA products (or amplification products thereof). Numerous technological platforms for performing high throughput expression analysis using nucleic acid arrays are available. Common array formats include both liquid and solid phase arrays. For example, assays employing liquid phase arrays, e.g., for hybridization of nucleic acids, can be performed in multiwell, or microtiter, plates. Microtiter plates with 96, 384 or 1536 wells are widely available, and even higher numbers of wells, e.g, 3456 and 9600 can be used. In general, the choice of microtiter plates is determined by the methods and equipment, e.g., robotic handling and loading systems, used for sample preparation and analysis. Exemplary systems include, e.g., the ORCA™ system from Beckman-Coulter, Inc. (Fullerton, Calif.) and the Zymate systems from Zymark Corporation (Hopkinton, Mass.).

Alternatively, a variety of solid phase arrays can favorably be employed to determine expression profiles in the context of the present invention. Exemplary formats include membrane or filter arrays (e.g., nitrocellulose, nylon), pin arrays, and bead arrays (e.g., in a liquid "slurry"). Typically, nucleic acids corresponding to expressed RNA samples are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly) tetrafluoroethylene, (poly)vinylidenedifluoride, polystyrene, polycarbonate, or combinations thereof can all serve as the substrate for a solid phase array. Coated forms of these materials (e.g., glass coated with polyamine, polyacrylamide, polythymidine or other functionalization) leads to improved non-covalent or covalent binding. The substrate can be a single contiguous surface, e.g. a plate or multiple discrete surfaces, e.g. etched plates, filters, or optical fiber ends. Alternatively, the array can be composed of a series of beads that can be discretely identified via a number of either color coding schemes (e.g., see products manufactured by Luminex Corporation; Austin, Tex.) and flow cytometry or means to physically trap the beads on a surface (e.g., see products manufactured by Illumina, Inc., San Diego, Calif.; and Lynx Therapeutics, Inc., Hayward, Calif.). Techniques for the creation and use of these arrays are known to those skilled in the art.

In a preferred embodiment, the array is a "chip" or "slide" composed, e.g., of one of the above specified materials, such as a glass microarray slide. Most commonly, nucleic acid samples corresponding to expressed RNA samples are deposited, e.g., "spotted" onto the chip or slide to produce a spatial array in which each distinct nucleic acid population corresponding to a different expressed RNA sample (e.g., derived from a different biological sample) is assigned a unique location on the microarray surface.

Application of nucleic samples to the substrate can be performed using automated devices, or manually, for example, using a multipin, e.g., 32 pin tool, with an alignment device (e.g., Xenopore, that can deposit up to 768 6 nl spots onto a glass slide). Detailed discussion of methods for linking nucleic acids to a substrate, are found in, e.g., U.S. Pat. No. 5,837,832 "Arrays of Nucleic Acid Probes on Biological Chips" to Chee et al., issued Nov. 17, 1998; U.S. Pat. No. 6,087,112 "Arrays with Modified Oligonucleotide and Polynucleotide Compositions" to Dale, issued Jul. 11, 2000; U.S. Pat. No. 5,215,882 "Method of Immobilizing Nucleic Acid on a Solid Substrate for Use in Nucleic Acid Hybridization Assays" to Bahl et al., issued Jun. 1, 1993; U.S. Pat. No. 5,707,807 "Molecular Indexing for Expressed Gene Analysis" to Kato, issued Jan. 13, 1998; U.S. Pat. No. 5,807,522 "Methods for Fabricating Microarrays of Biological Samples" to Brown et al., issued Sep. 15, 1998; U.S. Pat. No. 5,958,342 "Jet Droplet Device" to Gamble et al., issued Sep. 28, 1999; U.S. Pat. 5,994,076 "Methods of Assaying Differential Expression" to Chenchik et al., issued Nov. 30, 1999; U.S. Pat. No. 6,004,755 "Quantitative Microarray Hybridization Assays" to Wang, issued Dec. 21, 1999; U.S. Pat. No. 6,048,695 "Chemically Modified Nucleic Acids and Methods for Coupling Nucleic Acids to Solid Support" to Bradley et al., issued Ap. 11, 2000; U.S. Pat. No. 6,060,240 "Methods for Measuring Relative Amounts of Nucleic Acids in a Complex Mixture and Retreival of Specific Sequences Therefrom" to Kamb et al., issued May 9, 2000; U.S. Pat. No. 6,090,556 "Method for Quantitatively Determining the Expression of a Gene" to Kato, issued Jul. 18, 2000; U.S. Pat. No. 6,040,138 "Expression Monitoring by Hybridization to High Density Oligonucleotide Arrays" to Lockhart et al., issued Mar. 21, 2000; NHGRI Microarray Project Protocols: on the world wide web at nhgri.nih.gov/DIR/HMicroarray/protocols.html; MacGregor P, Microarray protocol: on the world wide web at uhnres.utoronto.ca/services/microarray/download/protocols/procol_edward.pdf; and Hedge et.al. (2000) Biotechniques 29: 548-562.

As the number of probes to be hybridized (i.e., the number of genes or sequences to be analyzed) increases, it is often desirable to produce replicate or copies of the microarray. The following illustrates one exemplary automatable array copying format, e.g., for producing replicate microarrays incorporating copies of the nucleic acids corresponding to RNA expression products from biological samples. For example, arrays can be copied in an automated format to produce duplicate arrays, master arrays, amplified arrays and the like, e.g., where repeated hybridization and washing of defined sequence probes makes recovery or detection of nucleic acids from an original array problematic (e.g. where a process to be performed destroys the original nucleic acids or attenuates the signal). Copies can be made from master arrays, reaction mixture arrays or any duplicates thereof.

For example, nucleic acids (e.g., a plurality of expressed RNA samples from biological sources) can be dispensed into one or more master multiwell plates and, typically, amplified to produce a master array of amplified nucleic acids (e.g., by PCR) to produce an array of amplification products. The array copy system then transfers aliquots from the wells of the one or more master multiwell plates to one or more copy multiwell plates. Typically, a fluid handling system will deposit copied array members in destination locations, although non-fluid based member transport (e.g., transfer in a solid or gaseous phase) can also be performed.

Arraying techniques for producing both master and duplicate arrays from populations of nucleic acids can involve any of a variety of methods. For example, when forming solid phase arrays (e.g., as a copy of a liquid phase array, or as an original array), members of the population can by lyophilized or baked on a solid surface to form a solid phase array, or chemically coupled or printed (e.g., using ink-jet printing or chip-masking and photo-activated synthesis methods) to the solid surface.

Expression Profiling

The plurality of probes (e.g., set of genes or gene products) selected for analysis can be selected, for example, by reviewing known scientific literature or by performing empirical studies. In one embodiment, the probes are selected from among genes (or gene products) that are (a) expressed at detectable levels within the biological samples, and (b) are likely to change as a result of exposure to one or more member compositions. Two types of genes (or their respective gene products) are typically monitored during generation of the genetic response profile: genes that are empirical responders (i.e. marker genes) and genes that are known or suspected to be involved in the pathways or disease area of interest (i.e., disease related genes). Optionally, one or more genes known to be affected by at least one composition in the set of compounds or chemicals are monitored (e.g., a positive control).

Typically, a moderate to large number of genes (i.e., expressed RNAs) are selected for analysis, i.e., expression (or response) profiling. Such a set of genes commonly includes at least three polynucleotide sequences, more commonly between about 10 and about 20 sequences, often about 50 sequences, sometimes about 100, and occasionally as many as about 1000, or more individual polynucleotide sequences, e.g., corresponding to different or distinct genes. Nucleic acid sequences that can be monitored in the methods of the present invention include, but are not limited to, those listed with the National Center for Biotechnology Information (on the world wide web at ncbi.nlm.nih.gov) in the GenBank® databases, and sequences provided by other public or commercially-available databases (for example, the NCBI EST sequence database, the EMBL Nucleotide Sequence Database; Incyte's (Palo Alto, Calif.) LifeSeq™ database, and Celera's (Rockville, Md.) "Discovery System"™ database). For example, nucleic acids that can be monitored (e.g., as part of the genetic response profile) according to the methods of the present invention include, nucleic acids encoding proteins including, but not limited to, signaling proteins, regulatory proteins, pathway specific proteins, receptor proteins, and other proteins involved in one or more biochemical pathways.

Analysis of Gene Expression Data

Profiles of gene expression in expressed RNA samples can be evaluated by either (or both) qualitative and quantitative measures. Certain of the above described techniques for evaluating gene expression (as RNA or protein products) yield data that are predominantly qualitative in nature. That is, the methods detect differences in expression that classify expression into distinct modes without providing significant information regarding quantitative aspects of expression. For example, a technique can be described as a qualitative technique if it detects the presence or absence of expression of a candidate gene, i.e., an on/off profile of expression. Alternatively, a qualitative technique measures the presence (and/or absence) of different alleles, or variants, of a gene product.

In contrast, some methods provide data that characterizes expression in a quantitative manner. That is, the methods relate expression on a numerical scale, e.g, a scale of 0-5, a scale of 1-10, a scale of + to +++, from grade 1 to grade 5, a grade from a to z, or the like. It will be understood that the numerical, and symbolic examples provided are arbitrary, and that any graduated scale (or any symbolic representation of a graduated scale) can be employed in the context of the present invention to describe quantitative differences in gene expression. Typically, such methods yield information corresponding to a relative increase or decrease in expression.

Any method that yields either quantitative or qualitative expression data is suitable for evaluating signals corresponding to hybridization between a defined sequence probe, e.g., corresponding to a gene, such as a disease related gene) and an arrayed nucleic acid sample. In some embodiments, it is useful to quantitate the level of expression of a gene relative to other expression products, and/or relative to a control sequence. One convenient and broadly applicable method of determining relative expression and hybridization levels between expression products on an array, as well as between physical arrays, is to compare the expression of one or more genes of interest to the expression of a control gene, such as a housekeeping gene (e.g., HSP 70, β-actin, etc.) One or more defined sequence probes specific for the genes of interest are hybridized along with a probe specific for the selected housekeeping gene. Hybridization to each of the probes is detected and quantitated. Then the hybridization signal corresponding to the genes of interest is compared to that for the housekeeping gene. Expression can then be expressed relative to that of the housekeeping gene which is expected to be approximately constant within and between samples.

In order to ascertain whether the observed expression data, e.g., a change in expression profiles in response to one or more treatments of a biological sample, are significant, and not just a product of experimental noise or population heterogeneity, an estimate of a probability distribution can be constructed for each genetic and phenotypic endpoint in each biological sample. Construction of the estimated population distribution involves running multiple independent experiments for each treatment, e.g. all experiments are run in duplicate, triplicate, quadruplicate or the like.

Analysis of the data involves the use of a number of statistical tools to evaluate the measured expression as extrapolated from the hybridization signal, e.g., responses and changes resulting from one or more treatment of a biological sample, based on type of change, direction of change, shape of the curve in the change, timing of the change and amplitude of change.

Multivariate statistics, such as principal components analysis (PCA), factor analysis, cluster analysis, n-dimensional analysis, difference analysis, multidimensional scaling, discriminant analysis, and correspondence analysis, can be employed to simultaneously examine multiple variables for one or more patterns of relationships (for a general review, see Chatfield and Collins, *Introduction to Multivariate Analysis*, published 1980 by Chapman and Hall, New York; and Hoskuldsson Agnar, *Predictions Methods in Science and Technology*, published 1996 by John Wiley and Sons, New York). Multivariate data analyses are used for a variety of applications involving these multiple factors, including quality control, process optimization, and formulation determinations. The analyses can be used to determine whether there are any trends in the data collected, whether the properties or responses measured are related to one another, and which properties are most relevant in a given context (for example, a disease state). Software for statistical analysis is commonly available, e.g., from Partek Inc. (St. Peters, Mo.; see www.partek.com).

One common method of multivariate analysis is principal component analysis (PCA, also known as a Karhunen-Loeve expansion or Eigen-XY analysis). PCA can be used to transform a large number of (possibly) correlated variables into a smaller number of uncorrelated variables, termed "principal components." Multivariate analyses such as PCA are known to one of skill in the art, and can be found, for example, in Roweis and Saul (2000) *Science* 290:2323-2326 and Tenenbaum et al. (2000) *Science* 290:2319-2322. Several methods of constructing and analyzing dataspace, e.g., including multivariate analysis are available. See, e.g., Hinchliffe (1996) *Modeling Molecular Structures* John Wiley and Sons, NY, NY; Gibas and Jambeck (2001) *Bioinformatics Computer Skills* O'Reilly, Sebastopol, Calif.; Pevzner (2000) *Computational Molecular Biology and Algorithmic Approach*, The MIT Press, Cambridge Mass.; Durbin et al. (1998) *Biological Sequence Analysis: Probabilistic Models of Proteins and Nucleic Acids*, Cambridge University Press, Cambridge, UK; Rashidi and Buehler (2000) *Bioinformatic Basics: Applications in Biological Science and Medicine*, CRC Press LLC, Boca Raton, Fla.; and Mount (2001) *Bioinformatics: Sequence and Genome Analysis*, Cold Spring Harbor Press, NY.

The expression data from multiple biological samples can be grouped, or clustered, using multivariate statistics. Clusters for each different stimulation (treating) and observation (detecting) experiment are compared and a secondary set of correlations/noncorrelations are made. Based on these different sets of correlations, a network map can be created wherein the relative relationships of the different genetic elements can be established as well as how they may act in concert. In addition, the data can be visualized using graphical representations. Thus, the temporal changes exhibited by the different biochemical and genetic elements within a genetically-related group of cells lines can be transformed into information reflecting the functioning of the cells within a given environment.

Different experimental outcomes are compared by the similarity of the pattern of expression profiles generated. This similarity is revealed using, for example, clustering analysis. A number of clustering algorithms are commonly used for this type of study (see J A Hartigan (1975) *Clustering Algorithms*, Wiley, N.Y.). The comparisons between profiles can be performed at the level of individual genes, clusters of genes known to be involved in specific pathways or mechanisms, individual cell lines, or for the entire experimental data set. For example, for each experimental pair, e.g. two different composition treatment sets, a distance metric can be defined as $D=1-\rho$, where $\rho$ is the correlation coefficient between the expression profiles. The value of D indicates the level of similarity between two experimental pairs. In this manner, a matrix can be created wherein chemicals producing similar profiles closely cluster, i.e. D is small, and those with divergent profiles will have large D values. This type of analysis can reveal, for example, similarities in the mechanism of response of various chemicals. Furthermore, analysis among similar cell types and between different cell types is used to determine what cell, tissue, organ or tumor types may be more or less vulnerable when exposed to a given chemical.

Nucleic Acid Hybridization

Following production of an array of nucleic acid corresponding to expressed RNA products, expression is evaluated for a set of probes. Each of the probes in a set is composed of a unique defined sequence of polynucleotides. Different members of a probe set can be either related or unrelated polynucleotide sequences, and commonly correspond to polynucleotide sequences associated with disease related genes or targets. Frequently, the defined sequence probes are synthetic oligonucleotides, although alternative synthetic probes are also suitable, e.g., cDNA probes, restriction fragments, amplification products, and the like. Hybridization of the plurality of defined sequence probes occurs in a single reaction mixture (hybridization mixture).

Generally, but not exclusively, the defined sequence probes are not themselves labeled. Generally, hybridization products formed following application of the amplified RNA sample to the array are visualized by global labeling of the amplified RNA products, typically prior to the hybridization reaction. One exception to this generalization is the use of molecular-beacon type probes (see the products manufactured by, for example, Gen-Probe, Inc., San Diego, Calif.). One of skill in the art will recognize the many variations of microarray technology, all of which find use with and are within the scope of the claimed invention.

In some microarray embodiments, a plurality of labeled species are simultaneously analyzed on the same microarray. Differential detection of the different labeled hybridization complexes is made possible by the inclusion of a different label or signal generating moiety. For example, different defined sequence probes to be analyzed simultaneously in a single hybridization reaction can include different fluorescent labels which can be distinguished on the basis of their emission spectra. Alternatively, each defined sequence probe can incorporate an amplifiable signal element, e.g., an oligonucleotide sequence which can be amplified in a subsequent amplification reaction incorporating a fluorescent or other detectable moiety.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid*

Probes, part I, chapter 2, "Overview of principles of hybridization and the strategy of nucleic acid probe assays," (Elsevier, NY), as well as in Ausubel, supra. Hames and Higgins (1995) *Gene Probes* 1. IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

"Stringent hybridization wash conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched primer. Very stringent conditions are selected to be equal to the $T_m$ for a particular primer.

The Tm is the temperature of the nucleic acid duplexes indicates the temperature at which the duplex is 50% denatured under the given conditions and its represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides.

After hybridization, unhybridized nucleic acid material can be removed by a series of washes, the stringency of which can be adjusted depending upon the desired results. Low stringency washing conditions (e.g., using higher salt and lower temperature) increase sensitivity, but can product non-specific hybridization signals and high background signals. Higher stringency conditions (e.g., using lower salt and higher temperature that is closer to the hybridization temperature) lowers the background signal, typically with only the specific signal remaining. See, Rapley, R. and Walker, J. M. eds., *Molecular Biomethods Handbook* (Humana Press, Inc. 1998) (hereinafter "Rapley and Walker"), which is incorporated herein by reference in its entirety for all purposes.

Thus, one measure of stringent hybridization is the ability of the probe to hybridize to one or more of the target nucleic acids (or complementary polynucleotide sequences thereof) under highly stringent conditions. Stringent hybridization and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions are gradually increased until a target nucleic acid, and complementary polynucleotide sequences thereof, binds to a perfectly matched complementary nucleic acid.

A target nucleic acid is said to specifically hybridize to a probe (or primer) nucleic acid when it hybridizes at least ½ as well to the probe as to a perfectly matched complementary target, i.e., with a signal to noise ratio at least ½ as high as hybridization of the probe to the target under conditions in which the perfectly matched probe binds to the perfectly matched complementary target with a signal to noise ratio that is at least about 2.5×-10×, typically 5×-10× as high as that observed for hybridization to any of the unmatched target nucleic acids.

Labels

In the methods of the present invention, multiple probes, each of defined sequence, and each of which is capable of giving rise to a different detectable signal, are hybridized simultaneously, i.e., in a single reaction, to a nucleic acid array. In one favorable embodiment, the probes are each labeled with a different fluorescent chromaphore. A fluorescent label may be covalently attached, noncovalently intercalated, or may be an energy transfer label. Other useful labels include mass labels, which are incorporated into amplification products and released after the reaction for detection, chemiluminescent labels, electrochemical and infrared labels, isotopic derivatives, nanocrystals, or any of various enzyme-linked or substrate-linked labels detected by the appropriate enzymatic reaction.

One preferred embodiment of the methods of the present invention includes the use and detection of one or more fluorescent labels. Generally, fluorescent molecules each display a distinct emission spectrum, thereby allowing one to employ a plurality of fluorescent labels in a single mixed probe reaction, and then separate the mixed data into its component signals by spectral deconvolution. Exemplary fluorescent labels for use in the methods of the present invention include a single dye covalently attached to the molecule being detected, a single dye noncovalently intercalated into product DNA, or an energy-transfer fluorescent label. Numerous suitable combinations of fluorescent labels are known in the art, and available from commercial sources (e.g., Molecular Probes, Eugene Oreg.; Sigma, St. Louis, Mo.).

For example, fluorescent moieties, including Alexa Fluor 350, Alexa Fluor 405, Alexa Fluor 430, Alexa Fluor 488, Alexa Fluor 532, Alexa Fluor 532, Alexa Fluor 546, Alexa Fluor 555, Alexa Fluor 568, Alexa Fluor 594, Alexa Fluor 647, Alexa Fluor 660, Alexa Fluor 680, AMCA, BODIPY 630/650, BODIPY 650/665, BODIPY-FL, BODIPY-R6G, BODIPY-TMR, BODIPY-TRX, carboxyfluorescein, Cascade Blue, Cy3, Cy5, Cy5.5, 6-FAM, Fluorescein, HEX, 6-JOE, Lissamine rhodamine B, Oregon Green 488, Oregon Green 500, Oregon Green 514, Pacific Blue, REG, Rhodamine Green, Rhodamine Red, ROX, SpectrumAqua, TAMRA, TET, Tetramethylrhodamine, and Texas Red, are generally known in the art and routinely used for identification of discreet nucleic acid species, such as in sequencing reactions. One of skill in the art, can easily select dyes having different emission spectra, enabling detection of differently labeled probes hybridized to the same nucleic acid array. One suitable combination compatible with many common lasers and filters includes, e.g., Fluorescein, Texas Red, Cy3, and Cy5, or a combination of, e.g., Alex Fluor dyes according to the manufacturer's instructions (Molecular Probes, Eugene, Oreg.).

The signal strength obtained from fluorescent dyes can be enhanced through use of related compounds called energy transfer (ET) fluorescent dyes. After absorbing light, ET dyes have emission spectra that allow them to serve as "donors" to a secondary "acceptor" dye that will absorb the emitted light and emit a lower energy fluorescent signal. Use of these coupled-dye systems can significantly amplify fluorescent signal. Examples of ET dyes include the ABI PRISM BigDye terminators, recently commercialized by Perkin-Elmer Corporation (Foster City, Calif.) for applications in nucleic acid analysis. These chromaphores incorporate the donor and acceptor dyes into a single molecule and an energy transfer linker couples a donor fluorescein to a dichlororhodamine acceptor dye, and the complex is attached to a DNA replication primer. Alternatively, signals corresponding to hybridization of a probe to a nucleic acid can be amplified using anti-dye antibodies, or enzyme mediated amplification strategies, such as tyramide signal amplification and enzyme labeled fluorescence (ELF) technologies (Molecular Probes, Eugene, Oreg.: additional details can be found in the Molecular Probes handbook and in product literature).

Enzyme-linked reactions theoretically yield a robust signal due to amplification of the signal by enzymatic activity. In this embodiment, an enzyme is linked to a secondary group that has a strong binding affinity to the molecule of interest. Following hybridization of an enzyme linked probe to the nucleic acid array, hybridization is detected by a chemical reaction catalyzed by the associated enzyme. Various coupling strategies are possible utilizing well-characterized interactions generally known in the art, such as those between biotin and avidin, an antibody and antigen, or a sugar and lectin. Various types of enzymes can be employed, generating calorimetric, fluorescent, chemiluminescent, phosphorescent, or other types of signals. Following hybridization to an enzyme-linked probe, a chemical reaction is conducted, detecting bound enzyme by monitoring the reaction product. The secondary affinity group may also be coupled to an enzymatic substrate, which is detected by incubation with unbound enzyme. One of skill in the art can conceive of many possible variations on enzyme linked labeling methods.

Alternatively, technologies such as the use of nanocrystals as a fluorescent DNA label (Alivisatos, et al. (1996) Nature 382:609-11) can be employed in the methods of the present invention. Another method, described by Mazumder, et al. (Nucleic Acids Res. (1998) 26:1996-2000), describes hybridization of a labeled oligonucleotide probe to its target without physical separation from unhybridized probe. In this method, the probe is labeled with a chemiluminescent molecule that in the unbound form is destroyed by sodium sulfite treatment, but is protected in probes that have hybridized to target sequence.

Other embodiments of labeling include mass labels, which are incorporated into amplification products and released after the reaction for detection; chemiluminescent, electrochemical, and infrared labels; radioactive isotopes; and any of various enzyme-linked or substrate-linked labels detectable by the appropriate enzymatic reaction. Many other useful labels are known in the art, and one skilled in the art can envision additional strategies for labeling amplification products of the present invention.

Alternatively, a probe suitable for use in a microarray system can include an amplifiable signal element, for example a polynucleotide sequence which can serve as the template in a subsequent amplification reaction, such as a rolling circle amplification (RCA); ramification amplification (RAM); branched DNA amplification (BDA); hybridization signal amplification method (HSAM); and 3DNA dendrimer probes (Genisphere, Hatfield, Pa.). Additional methods for amplifying a signal include those described in, e.g., U.S. Pat. Nos. 6,251,639 and 5,545,522. The use of defined sequence probes incorporating amplifiable signal elements is particularly favored when the array comprises RNA or cDNA corresponding to expressed nucleic acids.

Detection Methods

Following hybridization of the defined sequence probes to the nucleic acid array, hybridization between the probes and the nucleic acids of the array is detected and/or detected, and optionally quantitated. Some embodiments of the methods of the present invention enable direct detection of products. Other embodiments detect reaction products via a label associated with one or more of the probes.

A variety of commercially available detectors, including, e.g., optical and fluorescent detectors, optical and fluorescent microscopes, plate readers, CCD arrays, phosphorimagers, scintillation counters, phototubes, photodiodes, and.the like, and software is available for digitizing, storing and analyzing a digitized video or digitized optical or other assay results, e.g., using PC (Intel x86 or pentium chip-compatible DOS™, OS2™ WINDOWS™, WINDOWS NT™ or WINDOWS95™ based machines), MACINTOSH™, or UNIX based (e.g., SUN™ work station) computers.

One described approach for quantifying fluorescence is to use a photomultiplier tube detector combined with a laser light scanner. Fluorescence imaging can also be performed using a charge-coupled device camera combined,e.g., with a UV light or xenon arc source. Fluorescent dyes with bimodal excitation spectra may be broadly implemented on a wide range of analytical imaging devices, permitting their widespread application to analysis of expression data (e.g., signals corresponding to hybridization between labeled probes and arrayed nucleic acids corresponding to expression products) in semiautomated analysis environments.

For example, the Perkin Elmer ScanArray Express microarray scanner, is capable of monitoring up to 5 dyes simultaneously, and is favorable employed in the methods of the present invention.

Screening Libraries of Compositions

The methods of the present invention are favorably employed for the purpose of identifying compounds, e.g., chemicals, that have a physiological effect on one or more physiological processes in a biological system, such as a cell (e.g., a cell line in culture), tissue or organism. In one favorable embodiment, a chemical or compound library is screened according to the methods of the invention. One favorable application of the present invention is in the screening of large compound libraries for the purpose of identifying agents with potential therapeutic application, e.g., activity relevant to a physiologic, metabolic or genetic pathway related to preventing or treating a disease state or condition. Alternative embodiments include screening compound libraries for compounds for purposes other than identifying therapeutic agents, e.g., agents with effects on a biological system unrelated to a disease state. Typically, biological samples, such as samples of a cell line in culture, are exposed to, or treated, e.g., contacted, with a member of a chemical or compound library. Following exposure, an expressed RNA sample is recovered from each treated sample, and analyzed as described herein. Typically, a large number of expressed RNA samples derived from biological samples, for example, a large number of samples each corresponding to a population of the same cell line, each of which has been treated with a different member of the compound library, are spatially arrayed, e.g., on a glass microarray slide and hybridized to a plurality of probes of interest, e.g., corresponding to genes encoding components of a biochemical pathway of interest. Usually, anywhere from about 100 (or 200, or 500) to several thousand, e.g., about 10,000, about 20,000 different expressed RNA samples corresponding to samples (i.e., populations) of a cell line, each of which is exposed to one (or more) members of a library of compositions, is arrayed and analyzed according to the methods of the invention.

For example, a cell or cell line can be treated with or exposed to one or more characterized or uncharacterized chemical libraries (chemical compound libraries), chemical or biochemical constituents, e.g., pharmaceuticals, pollutants, DNA damaging agents, oxidative stress-inducing agents, pH-altering agents, membrane-disrupting agents, metabolic blocking agent; a chemical inhibitors, cell surface receptor ligands, antibodies, transcription, promoters/enhancers/inhibitors, translation promoters/enhancers/inhibitors, protein-stabilizing or destabilizing agents, various toxins, carcinogens or teratogens, proteins, lipids, or nucleic acids. The libraries include combinatorial chemical libraries, scaffold-focused chemical libraries, target focused chemical libraries, biological libraries, natural product libraries, antisense agent libraries, iRNA libraries, siRNA libraries, ribozyme libraries, peptide libraries and combinatorial nucleic acid oligomer libraries, etc. As will be appreciated by one skilled in the art, the number of classes of compounds and/or compound analogues that can be screened for a physiological effect on a biological sample is extensive, and includes, but is not limited to, the following groups of compounds: ACE inhibitors; anti-inflammatory agents; anti-asthmatic agents; antidiabetic agents; anti-infectives (including but not limited to antibacterials, antibiotics, antifungals, antihelminthics, antimalarials and antiviral agents); analgesics and analgesic combinations; apoptosis inducers or inhibitors; local and systemic anesthetics; cardiac and/or cardiovascular preparations (including angina and hypertension medications, anticoagulants, anti-arrhythmic agents, cardiotonics, cardiac depressants, calcium channel blockers and beta blockers, vasodilators, and vasoconstrictors); chemotherapies, including various antineoplastics; immunoreactive compounds, such as immunizing agents, immunomodulators, immunosuppressives; appetite suppressants, allergy medications, arthritis medications, antioxidants, herbal preparations and active component isolates; neurologically-active agents including Alzheimers and Parkinsons disease medications, migraine medications, adrenergic receptor agonists and antagonists, cholinergic receptor agonists and antagonists, anti-anxiety preparations, anxiolytics, anticonvulsants, antidepressants, anti-epileptics, antipsycotics, antispasmodics, psychostimulants, hypnotics, sedatives and tranquilizers, and the like.

In some applications, selection of the compounds used for treatment of the biological samples is made based on literature and knowledge of experts in the field of interest. In order to take full advantage of the comparative analysis approach to discerning mechanism of response for a drug or composition and identifying new compositions, it is useful to analyze a selection of compositions including, but not limited to, a range of therapeutics (either approved or currently in clinical trials), therapeutic candidates, research chemicals, libraries of synthetic compositions, natural or biological compounds, herbal compositions, and other chemicals that potentially interact with one or more target molecules or that appear to drive cells to a comparable phenotype(s).

A number of tools and techniques can be used to treat cells in the context of the present invention. These techniques include, but are not limited to, transient treatments with chemicals that broadly stimulate activity and/or generally perturb the environment within the cell. By "stimulation" is meant a perturbation in the equilibrium state of the biochemical and/or genetic pathways of the cell, and is not meant to be limited to an increase in concentration or biological activity. Examples of stimulatory agents, chemicals and treatments include, but are not limited to, oxidative stress, pH stress, pH altering agents, DNA damaging agents, membrane disrupters, metabolic blocking agents, and energy blockers. Additionally, cellular perturbation may be achieved by treatment with chemical inhibitors, cell surface receptor ligands, antibodies, oligonucleotides, ribozymes and/or vectors employing inducible, gene-specific knock in and knock down technologies. The identity and use of stimulatory agents, chemicals and treatments are known to one of skill in the art.

Examples of DNA damaging agents include, but are not limited to, intercalation agents such as ethidium bromide; alkylating agents such as methyl methanesulfonate; hydrogen peroxide; UV irradiation, and gamma irradiation. Examples of oxidative stress agents include, but are not limited to, hydrogen peroxide, superoxide radicals, hydroxyl free radicals, perhydroxyl radicals, peroxyl radicals, alkoxyl radicals, and the like. Examples of membrane disrupters include, but are not limited to, application of electric voltage potentials, Triton X-100, sodium dodecyl sulfate (SDS), and various detergents. Examples of metabolic blocking and/or energy blocking agents include, but are not limited to, azidothymidine (AZT), ion (e.g. Ca++, K+, Na+) channel blockers, $\alpha$ and $\beta$ adrenoreceptor blockers, histamine blockers, and the like. Examples of chemical inhibitors include, but are not limited to, receptor antagonists and inhibitory metabolites/catabolites (for example, mavelonate, which is a product of and in turn inhibits HMG-CoA reductase activity).

Examples of cell surface receptor ligands include, but are not limited to, various hormones (estrogen, testosterone, other steroids), growth factors, and G-protein-coupled receptor ligands. Examples of antibodies include, but are not limited to, antibodies directed against TNF$\alpha$, TRAIL, or the HER2 growth factor receptor.

Examples of oligonucleotides that can be used to treat samples in present invention include, but are not limited to, ribozymes, anti-sense oligonucleotides, iRNA, siRNA, etc. For example, ribozymes are RNA molecules that have an enzymatic or catalytic activity against sequence-specific RNA molecules (see, for example, *Intracellular Ribozyme Applications: Principles and Protocols*, J. Rossi and L. Couture, eds. (1999, Horizon Scientific Press, Norfolk, UK)). Ribozymes can be generated against any number of RNA sequences, as shown in the literature for a number of target mRNAs including calretinin, TNF$\alpha$, HIV-1 integrase, and the human interleukins.

In one embodiment of the present invention, treating biological samples involves administering varying concentrations of the plurality of compounds to a plurality of biological samples (e.g., subpopulations of a cell line grown in culture), thereby generating a dose-response. The responses can be measured at either a single timepoint or over a plurality of timepoints. Optionally, at least one measurement is collected prior to treatment with the member composition. Commonly, this "zero time point" sample serves as a reference or control. Alternatively, or additionally, a separate but comparable biological sample (e.g., a subpopulation of the same cell line used for the treated samples) is left untreated or unexposed to any exogenous compound for purposes of a reference or control.

Systems for Gene Expression Analysis

The present invention also provides an integrated system for evaluating gene expression. The integrated system typically includes a logical or spatial array, e.g., a microarray organized on a glass slide, incorporating nucleic acid samples corresponding to a plurality of expressed RNA products derived from multiple biological sources or samples, e.g., cell lines, tissues, organ biopsies, organisms, etc. Optionally, the integrated system can include various components for preparation and collection of such biological samples, e.g., providing such functions as cell culture, most commonly in multi-well plates e.g., 96, 384, 768 or 1536 well plates (available from various suppliers such as VWR Scientific Products, West Chester, Pa.). Components and systems for automating the entire process, , e.g., sample and reagent pipetting, liquid dispensing, timed incubations, and final readings of the microplate in detector(s) are commercially available, and can be employed in the context of the systems of the present invention (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These configurable systems provide high throughput and rapid start up as well as a high degree of flexibility and customization. Similarly, arrays and array readers are available, e.g., from Affymetrix, PE Biosystems, and others.

The manufacturers of such systems provide detailed protocols the various high throughput. Thus, for example, Zymark Corp. provides technical bulletins describing screening systems for detecting the modulation of gene transcription, ligand binding, and the like.

For example, the system favorably includes a module for RNA isolation. Two commmercially available useful in the context of the present invention include platforms marketed by, Qiagen and GenoVision. Qiagen protocols using the 96-well RNeasy product and vacuum filtration can be performed using, e.g., a BioMek Multimek 96-tip pipetting system. This product and protocol isolates total RNA. Alternatively, the GenoVision GenoM-48 and GenoM-96 systems that are capable of isolating mRNA using polyT-conjugated magnetic beads for 48 or 96 samples at a time can be employed for RNA isolation from biological samples. Unlike the Qiagen process that requires user intervention to swap plates, the GenoVision process is fully automated.

The system typically includes an amplification module for producing a plurality of amplification products from a pool of expressed RNA products (e.g., expressed RNA products obtained from a biological sample); a detection module for detecting one or more members of the plurality of amplification products and generating a set of gene expression data; and an analyzing module for organizing and/or analyzing the data points in the data set. Any or all of these modules can comprise high throughput technologies and/or systems.

For example, the amplification module of the system of the present invention produces a plurality of amplification products from an expressed RNA sample. Optionally, the amplification module includes at least one pair of universal primers and at least one pair of target-specific primers for use in the amplification process, as described above. Furthermore, the amplification module can include components to perform one or more of the following reactions: a polymerase chain reaction (e.g., an rtPCR, a multiplex PCR, etc.), a transcription-based amplification, a self-sustained sequence replication, a nucleic acid sequence based amplification, a ligase chain reaction, a ligase detection reaction, a strand displacement amplification, a repair chain reaction, a cyclic probe reaction, a rapid amplification of cDNA ends, an invader assay, a bridge amplification, a rolling circle amplification, solution phase and/or solid phase amplifications, and the like.

The system also includes a hybridization module for contacting a plurality of differently labeled defined sequence probes with the nucleic acid microarray. The hybridization module commonly includes an incubation chamber or coverslip for maintaining conditions suitable for hybridization in solution of the plurality of probes with the nucleic acids disposed on the microarray. Optionally, the hybridization module accomodates additional reagents and reactions for amplifying the hybridization signal. Alternatively, a separate module is included for purposes of amplifying the hybridization signal.

The detection module detects the presence, absence, or quantity of hybridization between the plurality of probes and the microarray. Additionally, the detection module generates a set of gene expression data, generally in the form of a plurality of data points. Most commonly, the data points are recorded in a database. Typically, the data points are recorded in a computer readable medium, i.e., to generate a computer based database.

The third component of the system of the present invention, the analyzing module, is in operational communication with the detection module. The analyzing module of the system includes, e.g., a computer or computer-readable medium having one or more one or more logical instructions for analyzing the plurality of data points generated by the detection system. The analyzing system optionally comprises multiple logical instructions; for example, the logical instructions can include one or more instructions which organize the plurality of data points into a database and one or more instructions which analyze the plurality of data points. The instructions can include software for performing one or more statistical analyses on the plurality of data points. Additionally (or alternatively), the instructions can include or be embodied in software for generating a graphical representation of the plurality of data points. For example, Silicon Genetics' GeneSpring software is one suitable software program for use in the context of the present invention.

The computer employed in the analyzing module of the present invention can be, e.g., a PC (Intel x86 or Pentium chip-compatible DOS™, OS2™ WINDOWS™ WINDOWS NT™, WINDOWS95™, WINDOWS98™, or WINDOWS ME™), a LINUX based machine, a MACINTOSH™, Power PC, or a UNIX based machine (e.g., SUN™ work station) or other commercially common computer which is known to one of skill. Software for computational analysis is available, or can easily be constructed by one of skill using a standard programming language such as VisualBasic, Fortran, Basic, C, C++, Java, or the like. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can also be used in the analyzing system of the present invention.

The computer optionally includes a monitor that is often a cathode ray tube ("CRT") display, a flat panel display (e.g., active matrix liquid crystal display, liquid crystal display), or others. Computer circuitry is often placed in a box that includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for displaying and/or further analyzing raw data, massaged data, or proposed results from one or more computational processes involved in the analysis of the gene expression data set.

Kits

In an additional aspect, the present invention provides kits embodying the methods, compositions, and systems for analysis of gene expression as described herein. For example, a kit of the present invention can include one or more microarray slides (or alternative microarray format) onto which a plurality of different nucleic acid samples, each corresponding to an expressed RNA sample obtained from biological samples, e.g., samples treated with members of a compound library, have been deposited. The kit can also include a plurality of labeled probes. Alternatively, the kit can include a plurality of polynucleotide sequences suitable as probes and a selection of labels suitable for customizing the included polynucleotide sequences, or other polynucleotide sequences at the discretion of the practitioner. Commonly, at least one included polynucleotide sequence corresponds to a control sequence, e.g., β-actin, a "housekeeping" gene, or the like. Exemplary labels include, but are not limited to, a fluorophore, a dye, a radiolabel, an enzyme tag, etc., that is linked to a nucleic acid primer itself.

In one embodiment, kits that are suitable for amplifying nucleic acid corresponding to the expressed RNA samples are provided. Such a kit includes reagents and primers suitable for use in any of the amplification methods described above. Alternatively, or additionally, the kit are suitable for amplifying a signal corresponding to hybridization between a probe and a target nucleic acid sample (e.g., deposited on a microarray).

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing gene expression profiles using mRNA as the starting template. The mRNA template may be presented as either total cellular RNA or isolated mRNA; both types of sample yield comparable results. In other embodiments, the methods and kits described in the present invention allow quantitation of other products of gene expression, including tRNA, rRNA, or other transcription products.

Optionally, the kits of the present invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally comprise distinct containers for each individual reagent and/or enzyme component. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

EXAMPLES

The following examples are offered to illustrate, but not to limit the claimed invention.

Example 1

Amplification of an RNA Target using Multiplex, Universal Primer Driven PCR

Total RNA was obtained from culture cells using an RNA isolation kit (RNeasy®, Qiagen; Valencia, Calif.). Twenty ng of isolated RNA was then used first in a reverse transcription reaction, followed by a PCR amplification. These reaction conditions were as follows:

Reverse Transcription Reagents
Volume of Reaction: 20 μL
Gene Specific Reverse Primer Concentration: 0.05 μM (each primer)
Buffer Conditions: 1×PCR buffer II (10 mM Tris-HCl, pH 8.3; 50 mM KCl)
$MgCl_2$: 2.5 mM
dNTP's: 1 mM
DTT: 0.01M
RNase Inhibitor: 0.1U
MMLV Reverse transcriptase: 1U

| Thermal cycle conditions | |
| --- | --- |
| 48° C. | 1 minute |
| 37° C. | 5 minutes |
| 42° C. | 60 minutes |
| 95° C. | 5 minutes |
| 4° C. | end |

PCR Reagents
Volume of Reaction: 20 μL
Amount of cDNA used: 10 μL (of 20)
Chimeric Gene-Specific, Universal Forward Primers Concentration:
0.02 μM (each primer)
Buffer Conditions: 1× PCR buffer II (10 mM Tris-HCl, pH 8.3; 50 mM KCl)
$MgCl_2$: 7 mM
dNTP's: 0.3 mM
Universal Forward Primer Concentration: 1 μM
(labeled with fluorescent dye; e.g., Cy3 or Cy5)
Universal Reverse Primer Concentration: 1 μM
Taq polymerase: 2.5U

| Thermal cycle conditions | |
| --- | --- |
| 95° C. | 10 minutes |
| 94° C. | 30 seconds |
| 55° C. | 30 seconds |
| 68° C. | 1 minute |
| repeat steps 2-4 for 35 cycles | |
| 4° C. | end |

Microarray Printing

Oligonucleotide probes were received lyophilized and were diluted to a 100 µM stock solution in sterile water. Each oligonucleotide probe was diluted to a 10 µM working stock solution in a 96 well plate format. 10 µL of DMSO and 10 µL of the 10 µM oligonucleotide probe were pipetted into each well of the 384 well plate and mixed with the pipette. The plate is gently tapped on the counter top to make sure the 50% DMSO/oligonucleotide probe solution is in the bottom/center of the well where the spotting pins will dip into the well.

Prepared oligonucleotide probes were stored in 4° C. for short term storage and −20° C. for long term storage.

The working oligonucletides were then printed onto the microarray surface using a manual or automated microarray printing tool. Following printing and prior to hybridization, the printed microarray slide was baked at 85° C. for 1 hour to immobilize oligonucleotide DNA (single strand) on the slide. Slides were stored at this stage of processing at room temperature for use at a later date. The microarray was then incubated in a prehybridization solution (5×SSC, 0.1% SDS, 1% BSA) for one hour at room temperature on a shaker. The array was then washed with pure water and isopropanol. The microarray was then dried.

Hybridization of the UP-rtPCR Reactions to the Microarray

The fluorescently labeled PCR products were purified according to the manufacturer (Qiagen or Promega) instructions, and eluted into water, and mixed with 1× hybridization buffer (4×SSC, 0.02% Tween-20) and 90% glycerol, in a ratio of 5:39:6. The UP-rtPCR products were then denatured by heating the hybridization mixture at 95° C. for 5 minutes and snap cooled on ice for 30 sec. Multiple UP-rtPCR reactions were pooled during these steps.

The UP-rtPCR products were added to the microarray, covered, and then incubated at 50° C. for one hour.

Post-Hybridization Washes

Following hybridization, the microarray was washed, first in low stringency buffer (1×SSC and 0.2% SDS) at 55° C. for 30 minutes, and then in a high stringency buffer (0.1×SSC and 0.2% SDS) at 55° C. for three minutes. The microarray was then washed with water and dried in preparation for scanning.

Slide Scanning

Scanning was performed using a microarray scanning instrument (e.g. Axon Instruments, Union City, Calif., GenePix® microarray scanner) using the standard protocols recommended by the manufacturer. Data was then imported into a microarray data analysis software package, e.g., GeneSpring® (Silicon Genetics, Redwood City, Calif.).

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of determining two or more gene expression profiles comprising:
    obtaining RNA from two or more biological samples;
    amplifying the RNA from each of the two or more biological samples by rtPCR using at least one universal primer and at least one pair of chimeric gene-specific bar coded universal primers having a first sequence portion complementary to the universal primer, a second sequence portion complementary to a gene of interest, and a third sequence portion comprising a bar code sequence, thereby generating two or more sets of bar coded PCR products;
    providing an array comprising a set of nucleic acids representing a plurality of gene expression products, wherein members of the set of nucleic acids are positioned at discreet physical locations within the array, and wherein at least one member nucleic acid is complementary to the bar code sequence present in the two or more sets of bar coded PCR products;
    hybridizing members of the two or more sets of bar coded PCR products to the array, wherein the third sequence portion comprising the barcode sequence hybridizes to the complementary member nucleic acid of the array;
    washing the array and removing unbound bar coded PCR products; and,
    detecting and quantitating an amount of bar coded PCR product hybridized to a selected location within the array, thereby determining the gene expression profiles for each of the two or more biological samples.

2. The method of claim 1, wherein the at least one universal primer is a labeled universal primer.

3. The method of claim 2, wherein the labeled universal primer comprises a fluorescence label.

4. The method of claim 2, wherein the labeled universal primer comprises a radiolabel.

* * * * *